United States Patent
Yilmaz et al.

(10) Patent No.: US 10,112,177 B2
(45) Date of Patent: Oct. 30, 2018

(54) MATERIAL FOR AND METHOD OF EXTRACTING MYCOTOXINS

(71) Applicant: Biotage AB, Uppsala (SE)

(72) Inventors: Ecevit Yilmaz, Bjarred (SE); David Nivhede, Malmo (SE); Johan Billing, Lund (SE); Markus Rudolfsson, Horby (SE); Mats Leeman, Eslov (SE); Adam Senior, Cardiff (GB)

(73) Assignee: Biotage AB, Uppsala (SE)

( * ) Notice: Subject to any disclaimer, the term of this patent is extended or adjusted under 35 U.S.C. 154(b) by 298 days.

(21) Appl. No.: 14/780,307

(22) PCT Filed: Mar. 26, 2014

(86) PCT No.: PCT/EP2014/056088
§ 371 (c)(1),
(2) Date: Sep. 25, 2015

(87) PCT Pub. No.: WO2014/154766
PCT Pub. Date: Oct. 2, 2014

(65) Prior Publication Data
US 2016/0045894 A1 Feb. 18, 2016

(30) Foreign Application Priority Data

Mar. 27, 2013 (EP) .................. 13161362

(51) Int. Cl.
*C02F 1/28* (2006.01)
*B01D 15/00* (2006.01)
(Continued)

(52) U.S. Cl.
CPC ............ *B01J 20/267* (2013.01); *B01D 15/20* (2013.01); *B01J 20/261* (2013.01);
(Continued)

(58) Field of Classification Search
None
See application file for complete search history.

(56) References Cited

U.S. PATENT DOCUMENTS

| | | | |
|---|---|---|---|
| 4,933,372 A | 6/1990 | Feibush et al. | |
| 2006/0058413 A1* | 3/2006 | Leistner ............. | A61M 1/3679 523/105 |

(Continued)

FOREIGN PATENT DOCUMENTS

| | | | | |
|---|---|---|---|---|
| EP | 2189213 A1 * | 5/2010 | ......... | B01D 17/0202 |
| WO | WO-03101580 A1 | 12/2003 | | |
| WO | WO-2009/118401 A1 | 10/2009 | | |

OTHER PUBLICATIONS

Turner et al. (Biosensors and Bioelectronics, 2004, 20, 1060-1067). (Year: 2004).*

(Continued)

*Primary Examiner* — Clare M Perrin
(74) *Attorney, Agent, or Firm* — Harness, Dickey & Pierce, P.L.C.

(57) ABSTRACT

The present invention relates to a sorbent for extracting polar components from a sample where the sorbent comprises a cross-linked polymer comprising nitrogen containing cyclic compounds, for example 1-vinylimidazole and/or 4-vinylpyridine. The invention further relates to a method of producing said sorbent and the use of the sorbent.

13 Claims, 7 Drawing Sheets

(51) Int. Cl.
| | |
|---|---|
| C02F 1/68 | (2006.01) |
| B01J 20/26 | (2006.01) |
| C08F 271/02 | (2006.01) |
| C08F 291/00 | (2006.01) |
| C08F 226/00 | (2006.01) |
| B01J 20/32 | (2006.01) |
| B01J 20/30 | (2006.01) |
| B01J 20/28 | (2006.01) |
| B01D 15/20 | (2006.01) |
| C02F 1/00 | (2006.01) |
| C02F 5/08 | (2006.01) |
| C02F 5/10 | (2006.01) |
| B01D 15/02 | (2006.01) |
| G01N 1/40 | (2006.01) |
| G01N 30/00 | (2006.01) |

(52) U.S. Cl.
CPC ... *B01J 20/28019* (2013.01); *B01J 20/28042* (2013.01); *B01J 20/28052* (2013.01); *B01J 20/3092* (2013.01); *B01J 20/3293* (2013.01); *B01J 2220/62* (2013.01); *G01N 1/405* (2013.01); *G01N 2030/009* (2013.01)

(56) References Cited

U.S. PATENT DOCUMENTS

| | | |
|---|---|---|
| 2011/0054132 A1 | 3/2011 | Yiannikouris et al. |
| 2011/0089608 A1 | 4/2011 | Liu et al. |
| 2012/0214897 A1 | 8/2012 | Yiannikouris et al. |

OTHER PUBLICATIONS

Pekel et al. (Polymer Int., 2002, 51, 1404-1410) (Year: 2002).*
Weiss R et al., "Improving methods of; analysis for mycotoxins: Molecularly; imprinted polymers for deoxynivalenol and; zearalenone",Taylor and Francis, 2003, Food Additives and Contaminants,; vol. 20, No. 4, pp. 386-395, XP009017977.
Turner N W et al., "Effect of the solvent on recognition properties of molecularly imprinted polymer specific for ochratoxin A", Elsevier, 2004, Biosensors and Bioelectronics, Vo 20. pp. 1060-1067, XP004646746.
International Search Report PCT/ISA/210 for International Application No. PCT/EP2014/056088 dated Apr. 10, 2014.
Synthesis and characterization of poly (N-vinyl imidazole) hydrogels crosslinked by gamma irradiation; Nursel Pekel and Olgun Güven, Polymer International, vol. 51, No. 12; Dec. 1, 2002; pp. 1404-1410.
Communication pursuant to Article 94(3) EPC dated Jan. 12, 2017 issued in corresponding European Patent Application No. 13161362.2.

* cited by examiner

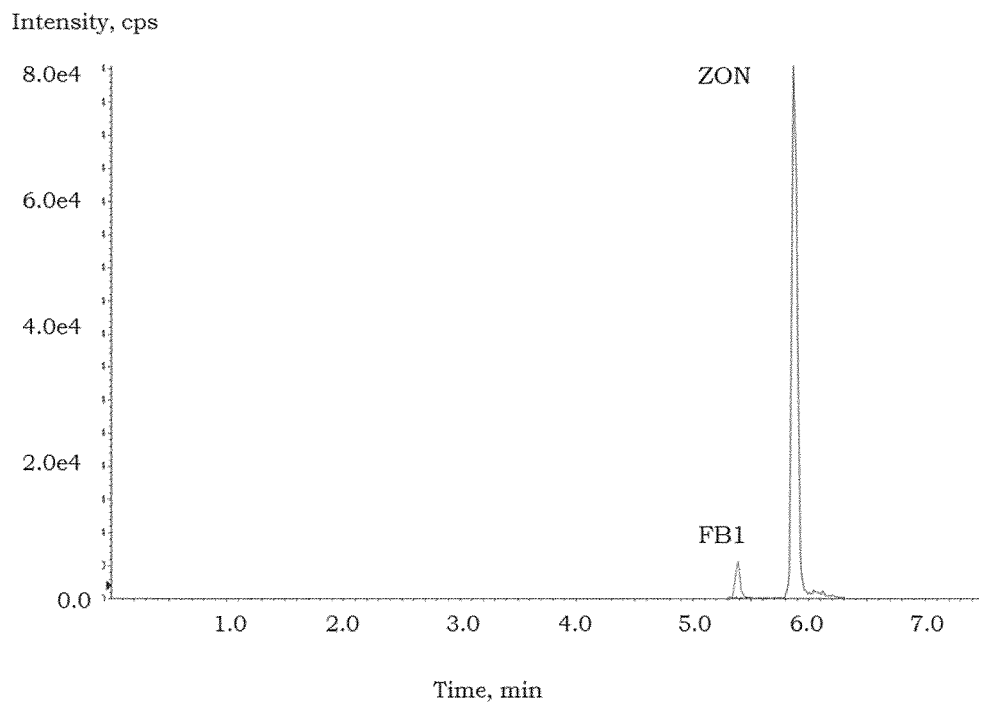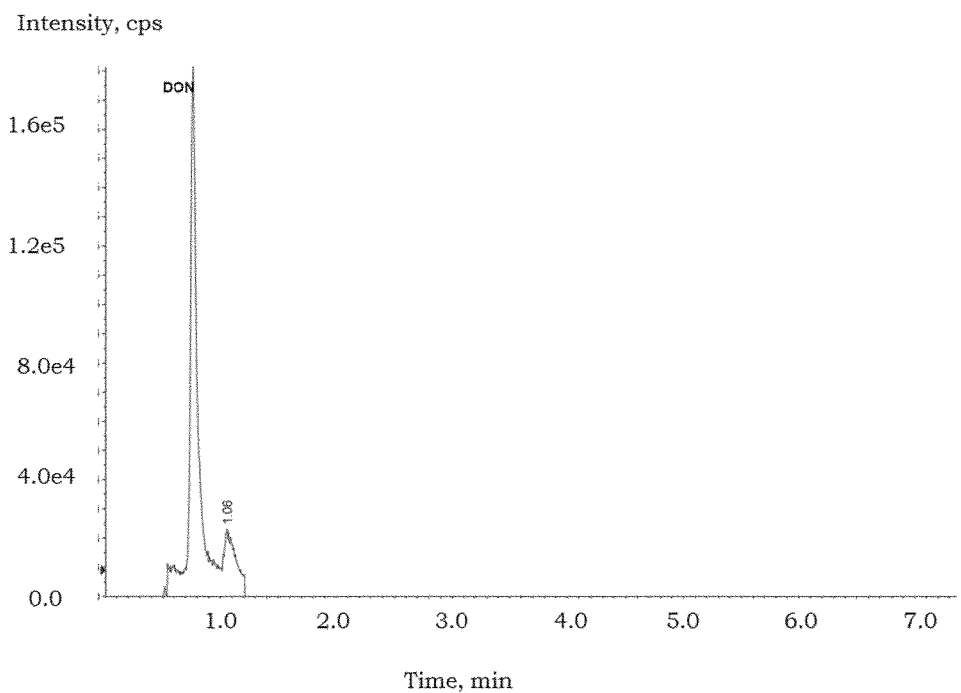
Figure 5.

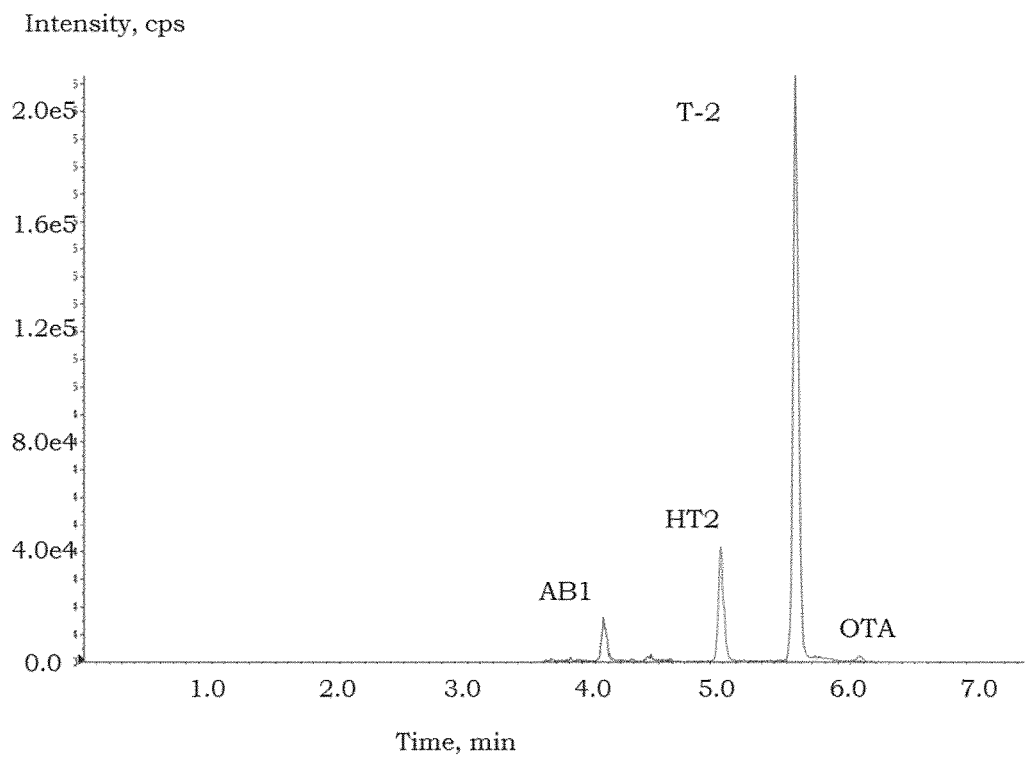
Figurer 6.
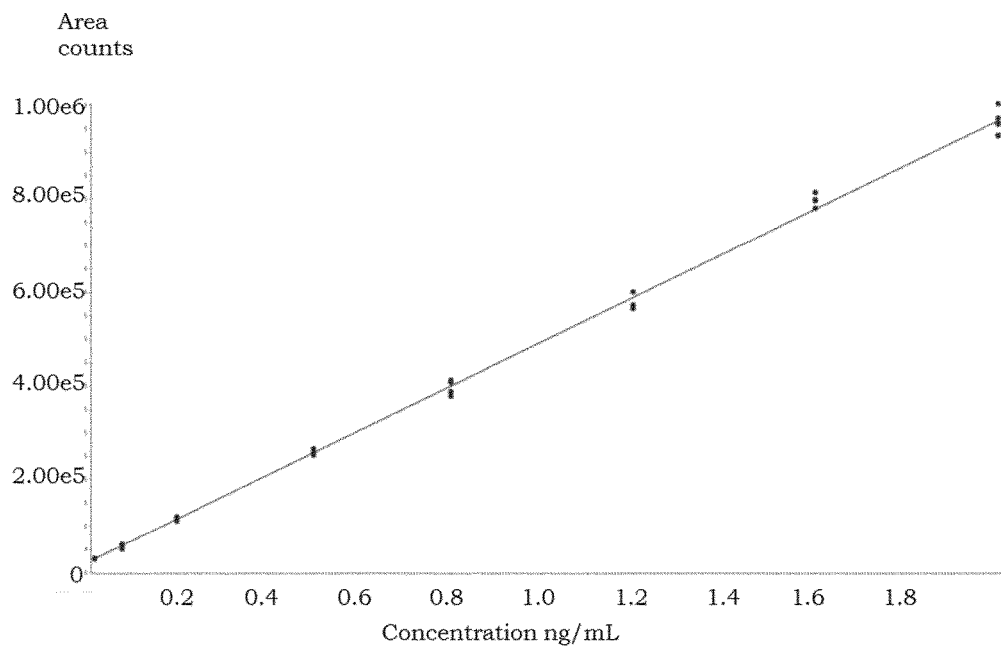
Figure 7.

MATERIAL FOR AND METHOD OF EXTRACTING MYCOTOXINS

CROSS-REFERENCE TO RELATED APPLICATIONS

This is a National Phase of PCT/EP2014/056088, filed on Mar. 26, 2014, which claims priority under 35 U.S.C. § 119.

FIELD OF THE INVENTION

The present invention relates to a material and a method of extracting polar compounds such as mycotoxins, and a method of making said material.

BACKGROUND

Solid-phase extraction (SPE) is a separation method where various dissolved or suspended compounds in a mixture are separated from other compounds in the mixture by bringing them into contact with a chemically defined solid phase material. The separation is based on the physical and chemical properties of the compounds and their ability to interact more or less strongly with the solid phase material. Analytical laboratories use solid phase extraction to concentrate and purify samples of specific compounds, or analytes, for analysis. Solid phase extraction can be used to isolate analytes of interest from a wide variety of matrices, including urine, blood, water, beverages, food, soil, and animal tissue.

In order to separate a mixture into desired and undesired components, SPE exploits the differences in affinity of individual solutes in a mixture that are dissolved or suspended in a liquid for a solid material, typically porous, through which the sample is passed (known as the solid phase). The result is that typically the desired analytes of interest and/or undesired impurities in the sample are retained on the solid phase during a loading stage. Subsequent exposure of the solid phase material to solvents or solvent mixtures of increasing elution 'strengths' leads to elution of the weakly bound material, typically impurities, followed by the analyte(s) of interest. The portion that passes through the solid phase is collected or discarded, depending on whether it contains the desired analyte(s) or undesired impurities.

When a polar compound in an aqueous medium is to be extracted a stationary phase containing non-polar functionalities may be employed, which may consist of short carbon chains bonded to an inorganic material such as silica or other hydrophobic entities chemically included in a polymer using appropriate monomers or compounds. This type of stationary phase will adsorb polar molecules which can then be eluted and collected as the eluting solvent polarity is progressively decreased.

Mycotoxins are toxic secondary metabolites produced by one or more species of spore-bearing fungi that colonize food crops in the field or food commodities post-harvest. Some species of fungi produce more than one mycotoxin and food products may be contaminated by more than one species. In addition to their toxicity, many mycotoxins have also been implicated as carcinogens and genotoxins. Mycotoxins exhibit a diverse range of chemical structures and associated physicochemical properties, creating significant challenges for their extraction and subsequent detection and quantitation. Regulation and legislation for testing of mycotoxin contamination has established which mycotoxins are globally significant for a variety of food products. EU regulations gives extensive details of the food contamination issues with mycotoxins and recommended limits of contamination, see 2006R1881:20100701.

Current methods for extraction of mycotoxins may employ specific anti-toxin antibodies, often used in immunoaffinity columns, or SPE with a hydrophilic lipophilic balanced (HLB) copolymers. The disadvantage of these methods is that extraction using antibodies is costly and sensitive to storage conditions, while HLB copolymers are inefficient due to problems with retaining the adsorbed mycotoxins during the washing procedures, especially when strong eluting solvents are used, resulting in unacceptably low recoveries.

WO03101580 discloses a method of binding mycotoxins to a solid carrier by contacting a mycotoxin containing solution, suspension or aerosol with a mycotoxin imprinted polymer and then separating the bound mycotoxin from the solution, suspension or aerosol.

EP2189213 discloses an adsorbent for removing toxicants from blood or plasma. The adsorbent comprises a divinyl benzene based porous bead where monomers or polymers are covalently linked to pendant vinyl groups of the porous bead leaving the monomers or polymers protruding from the bead surface. Suitable monomers may be primary, secondary or tertiary amines, for example 4-vinylimidazole and 2-vinylpyridine. According to the inventors of EP2189213, these monomers or polymers render the adsorbent more hemocompatible by minimizing the adsorption of proteins and cells on the surface of the adsorbents.

US20060058413 discloses a porous adsorbent material for removing albumin-bound toxins, drugs or pharmaceuticals. The adsorbent comprises 5-30 wt % of vinylimidazole monomers and 50 to 85 wt % of divinyl benzene.

SUMMARY OF THE INVENTION

In order to extract polar compounds such as mycotoxins using SPE, even when using strong eluting solvents, the stationary phase should preferably have a high affinity for the compound(s) to be extracted and bind to the compound(s) strongly enough to withstand the washing steps during which undesired impurities are removed.

In a first aspect the present invention relates to a solid-phase extraction sorbent having a core portion and an outermost portion, and wherein at least the outermost portion of the sorbent comprises a cross-linked polymer partly based on nitrogen containing cyclic compounds, such as nitrogen containing conjugated or non-conjugated cyclic compounds.

In a second aspect the present invention relates to the use of the sorbent of the present invention for extracting polar compounds.

In a third aspect the present invention relates to a method of extracting a polar compound from a sample using solid-phase extraction comprising:

- providing a sorbent according to the present invention;
- providing a sample in liquid phase;
- optionally equilibrating and wetting the sorbent using suitable solvent or solution;
- bringing the sorbent in contact with the sample in liquid phase allowing the compound to be extracted to bind to the sorbent;
- optionally washing the sorbent using one or more suitable solvents or solutions and optionally collecting the washed through samples; and
- optionally eluting the extracted polar compound using a suitable solvent or solution.

In a fourth aspect the present invention relates to a method of producing the sorbent according to the present invention comprising:

a) providing at least one nitrogen containing cyclic compound, such as nitrogen containing conjugated or non-conjugated cyclic compounds, a cross-linking agent, a solvent and a polymerisation initiator;
b) optionally providing pre-formed beads;
c) optionally providing a stabilizer;
d) mixing the components of step a) with the beads of step b) or with the stabilizer of step c);
e) allowing the mixture of step d) to polymerize; and
f) isolating the obtained sorbent.

In a fifth aspect the present invention relates to solid phase extraction cartridge comprising the sorbent according to the present invention.

In a sixth aspect the present invention relates to a separation column comprising the sorbent according to the present invention.

In a seventh aspect the present invention relates to a monolith comprising a cross-linked polymer partly based on nitrogen containing cyclic compounds, such as nitrogen containing conjugated or non-conjugated cyclic compounds.

All the embodiments described herein relate to all of the above mentioned aspects.

BRIEF DESCRIPTION OF FIGURES

FIG. 5, shows extracted ion chromatograms in negative ion mode using ISOLUTE Myco protocol at 100 µg $kg^{-1}$ from composite horse feed: a) FB1 and ZON using extraction conditions for mycotoxins excluding type B trichothecenes; b) DON using extraction conditions for type B trichothecenes.

FIG. 6, shows extracted ion chromatograms in positive ion mode using ISOLUTE Myco protocol at 5 µg $kg^{-1}$ (aflatoxin B1, ochratoxin A and T-2 toxin) and 100 µg µg $kg^{-1}$ (HT-2 toxin) from composite horse feed.

FIG. 7, shows Calibration curve for aflatoxin B1 from ground composite horse feed using the ISOLUTE Myco protocol from 0.02-2.0 ng $mL^{-1}$ FIG. 8, Calibration curve for HT-2 toxin from ground composite horse feed using the ISOLUTE Myco protocol from 2-200 ng $mL^{-1}$

DETAILED DESCRIPTION OF THE INVENTION

Figure 1:
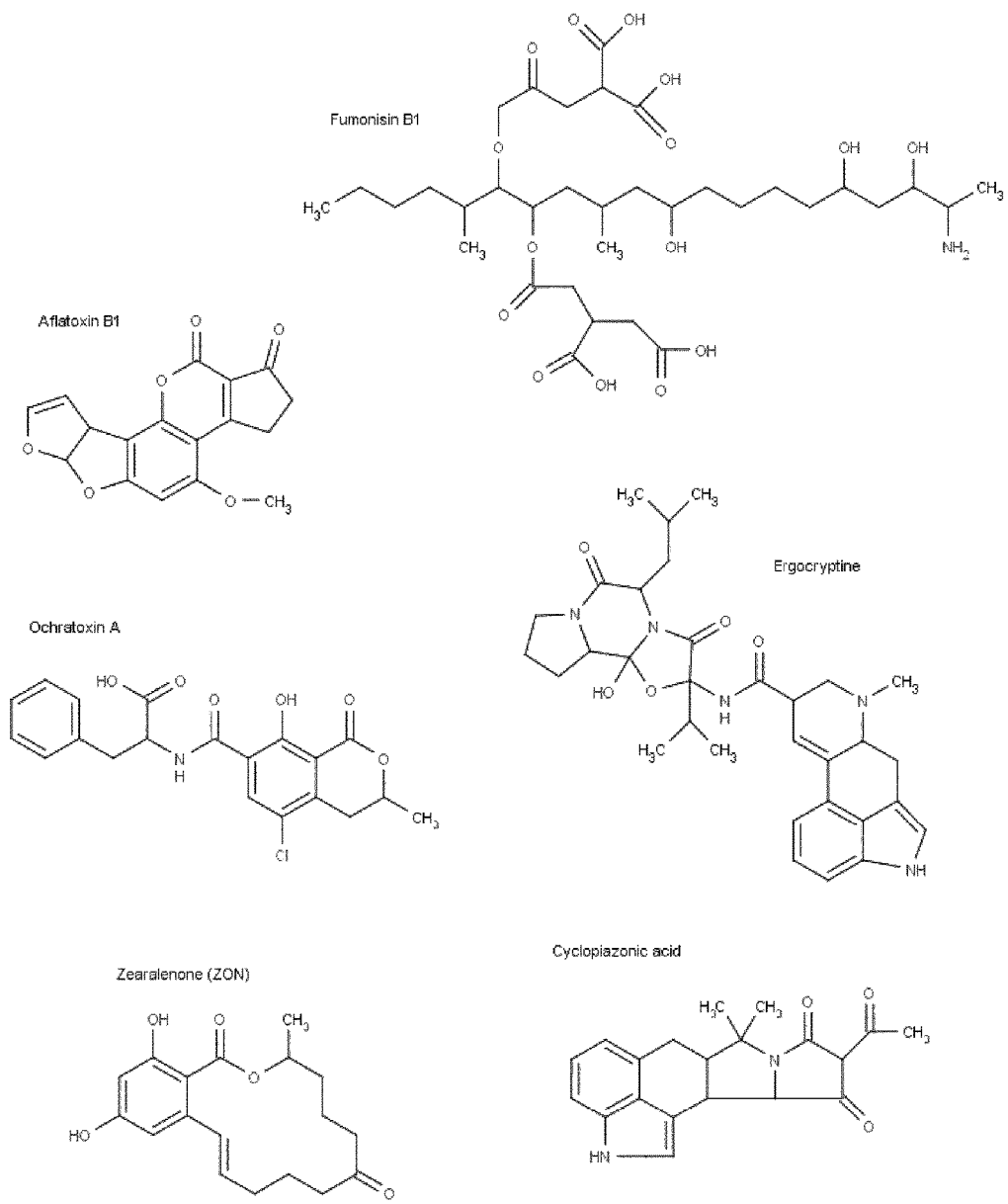
FIG. 1, chemical structure of various mycotoxins.

In the present invention the terms "nitrogen containing cyclic compounds" and "nitrogen containing cyclic monomers" mean the same thing and are used interchangeably.

Mycotoxins are often polar or highly polar and not easily extracted from aqueous solvents using common polymeric or silica based SPE solid phase materials (sorbents). When mycotoxins bind to the common SPE sorbents they typically bind with weak affinities which severely limits the discrimination between impurities and the desired analytes that can be achieved with common washing solvents.

The inventors of the present invention have found that a cross-linked polymeric resin comprising nitrogen containing cyclic compounds may be used for extracting polar or even highly polar compounds such as mycotoxins.

The cross-linked polymeric resin can be used as a solid phase extraction (SPE) sorbent on its own or in combination with other materials or other sorbents, and when the polar compound is bound to the sorbent in the presence of other impurities or matrix compounds, little or no loss of bound compound is observed during the washing steps. The sorbent material is much less costly to produce than the commonly used immunoaffinity sorbents and the material is superior to the other polymeric or silica-based sorbents commonly used for SPE and having affinity for and retaining polar compounds. The composition of the resin makes it possible to apply reasonably strong washing steps without risking premature elution of the extracted compound. This makes it possible to obtain higher purity of the sample since more washing steps or stronger eluting solvents can be used to remove unwanted components in the mixture while retaining the desired compound(s) on the SPE phase.

Furthermore, the resin may be used to remove mycotoxins from a liquid material such as a foodstuff or other material intended for human or animal consumption or other use in contact with humans or animals.

The SPE sorbent according to the present invention comprises a core portion and an outermost portion where at least the outermost portion of the sorbent comprises a cross-linked polymer partly based on nitrogen containing cyclic compounds. The core portion may in one embodiment comprise another material than the outermost portion or it may comprise the same material or a material also partly based on nitrogen containing cyclic compounds. In one embodiment the core portion comprises a pre-formed core bead.

The cross-linked polymer is partly based on nitrogen containing cyclic compounds which may be conjugated or non-conjugated and may be for example imidazole, pyridine, pyrrolidinone, pyrazine or pyrimidine based compounds. In one embodiment the nitrogen containing cyclic compound is aromatic. In one embodiment the nitrogen containing cyclic compound comprises a functional group susceptible to radical polymerization, for example the functional group can be a vinyl group, acrylic groups or allylic groups. Non-limiting examples of nitrogen containing cyclic compounds are 1-vinylimidazole, 4-vinylimidazole, 1-vinyl-2-methylimidazole, 1-vinyl-2-ethylimidazole, 1-propenyl-2-methylimidazole, 1-allyl-2-methylimidazole, 1-vinylpyridine, 2-vinylpyridine, 4-vinylpyridine, 2-methyl-5-vinylpyridine, N-vinyl-2-ethylimidazole, vinylpyrrolidinone and N-vinyl-2-ethylimidazole or mixtures thereof. In one embodiment the cross-linked polymer comprises 1-vinylimidazole or 4-vinylpyridine or a mixture thereof.

The cross-linked polymer may comprise a mixture of nitrogen containing cyclic compounds. The mixture may be a mixture of different co-polymers comprising two or more nitrogen containing cyclic compounds, for example 1-vinylimidazole or 4-vinylpyridine, or it may be a mixture of co-polymers comprising nitrogen containing cyclic compounds, for example 1-vinylimidazole and 4-vinylpyridine.

The total amount of nitrogen containing cyclic compounds in the outermost portion should be high enough to ensure affinity for the polar compound to be extracted and to retain the extracted compound during the washing steps. In one embodiment the weight ratio of nitrogen containing cyclic compounds to the core bead is at least 0.05, or at least 0.10, or at least 0.20, or at least 0.33 or at least 0.50. In one embodiment the weight ratio is at least 0.75, and in yet another embodiment the weight ratio is at least 1.

The total amount of nitrogen containing cyclic compounds in the cross-linked polymer is preferably 10 weight % or more, or 20 weight % or more, or 40 weight % or more, or 60 weight % or more, or 80 weight % or more, or 90 weight % or more. When the core portion of the sorbent comprises a bead of another material the amount of nitrogen containing cyclic compounds may be higher in comparison with when the core portion comprises the same material as the outermost portion or another material partly based on nitrogen containing cyclic compounds. When the core portion comprises a bead of another material the amount of nitrogen containing cyclic compounds in the outermost portion is preferably 60 weight % or more, or 80 weight % or more, or 90 weight % or more. When the core portion comprises the same material as the outermost portion or another material partly based on nitrogen containing cyclic compounds the amount may be 10 weight % or more, or 20 weight % or more.

A cross-linking agent is a component that promotes or regulates intermolecular covalent bonding between polymer chains. In one embodiment the polymer comprises a component or a monomer that can form cross-linking points for example by having two or more functional groups that can participate in the polymerization reaction, such a component being a cross-linking agent. Examples of such monomers are divinyl- or trimethacrylate-containing monomers such as divinyl benzene, dimethacrylates (EDMA), bis-acrylamides and trimethylolpropane trimethacrylate. Other examples of cross-linking agents are components that can be activated when exposed to heat or radiation such as various peroxides or vinylsilanes.

In one embodiment the core portion comprises a preformed bead. This bead may be of another material than the outermost portion, which makes the sorbent a composite, and may be polymeric or inorganic such as a silica bead. The polymeric bead may be based on divinyl benzene and styrene or on TRIM and MMA or on EDMA and MMA.

The sorbent of the present invention may be used to extract polar compounds from a sample. The compound can be a mycotoxin or any other polar or highly polar compound. In one embodiment the compound is selected from the group consisting of patulin, aflatoxin B1, B2, G1 and G2, ochratoxin, citrinin, ergot alkaloids, fusarium mycotoxins such as fumonisins, trichothecenes and zearalenone, ergocryptine and ergocornine. FIG. 1 discloses the chemical structure of some mycotoxins.

One method of extracting a polar compound from a sample using a sorbent according to the present invention comprises of providing a sample in liquid phase. In one embodiment the sample is in aqueous phase. Preferably the sorbent is equilibrated and wetted with a suitable solvent or solution prior to bringing the sample in contact with the sorbent. The compound to be extracted is allowed to bind to the sorbent followed by optional washing. The washing may be performed one or more times using the same or different solvents or solutions. The sample that is washed through may be collected. The extracted compound bound to the sorbent then may be eluted by washing the sorbent with a suitable solvent or solution.

Suitable solvents and solutions for equilibrating, wetting, washing and eluting may be alcohols such a methanol, ethanol, propanol, isopropanol, various buffers such ammonium acetate buffers, or acetonitrile, and mixtures of the same or with water. In one embodiment 10% isopropyl alcohol in water is used, and in another embodiment 20% isopropyl alcohol in water is used to wash the sorbent with the extracted compound. Acetonitrile may have a concentration of 5% or more in water, or 10% or more in water or 20% or more in water.

Any sample that can be transferred into liquid phase may be purified using the present invention. A non-limiting list of what can be tested or purified includes foodstuff, flour, wheat, maize, barley, nuts such as brazil nut and peanut, spices such as chili, beverages, soil, water, urine, blood and tissue.

Figure 2:
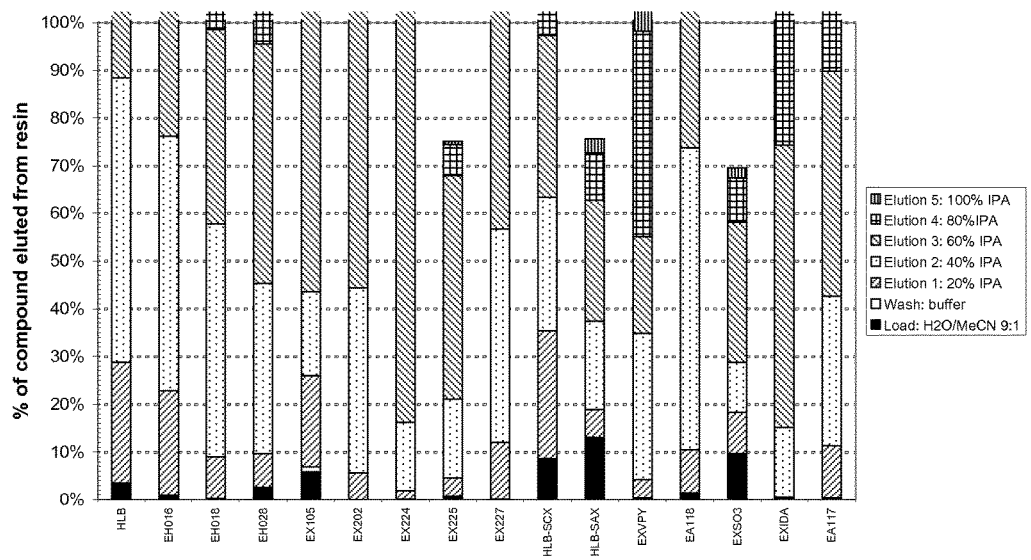
FIG. 2, shows a comparison of mycotoxin binding by different materials and washing steps. The numbers are the average for 12 different mycotoxins: Aflatoxin B1, Aflatoxin G1, Ergotamine, Ergocryptine, Ergocornine, Sterigmatocystin, Diacetoxyscirpenol, Ochratoxin A, Fumonisin B1, zearalenone (ZON), Cyclopiazonic acid and Citrinin.

FIG. 2 discloses a comparison of mycotoxin binding by different materials. EX224 and EXVPY contain 4-vinylpyridine and EX202 and EX225 contain 1-vinylimidazole. These polymers bind the mycotoxin more strongly than most materials and only very little is released even with 20% isopropyl alcohol. HLB can be considered representative for typical HLB materials and binds the mycotoxins much weaker with losses even in the loading step. EX227 and EXIDA IDA also bind the mycotoxins well, but are different types of materials. EX227 is an anion exchanger and EXIDA is a chelating resin.

The materials in FIG. 2 are:

| | |
|---|---|
| HLB | 20% NVP/0.2% EDMA/79.8% BB |
| EH016 | 6% 4-VPy/36% DVB/59% BB |
| EH018 | 5% 4-VPy/32% DVB/63% BB |
| EH028 | 4% 4-VPy/38% EDMA/58% BB |
| EX105 | 10% MAA/90% PETRA |
| EX202 | 9% 1-Vim/91% EDMA |
| EX224 | 24% 4-VPy/76% TRIM |
| EX225 | 22% 1-VIm/78% TRIM |
| EX227 | 7% 1-APip/93% TRIM |
| HLB-SCX | 7% AMPSA/24% NVP/6% DVB/63% BB |
| HLB-SAX | 2% VBTMAC/27% NVP/7% DVB/64% BB |
| EXVPY | 14% 4-Vpy/86% DVB |
| EA118 | 10% MAA/90% DVB |
| EXSO3 | 24% VBSO3H/76% DVB |
| EXIDA | 26% VBIDA/74% DVB |
| EA117 | 10% MAA/90% DVB |

The abbreviations above denote:
4-Vpy 4-vinyl-pyridine
1-Vim 1-vinyl-imidazole
DVB divinyl benzene
NVP N-vinyl-pyrrolidone
EDMA ethylene glycol dimethyl acrylate
MAA methacrylic acid
PETRA pentaerythriol triacrylate
TRIM trimethylolpropan trimethylacrylate
1-Apip 1-allyl-piperazine
AMPSA 2-acrylamido-2-methyl-1-propanesulfonic acid VBTMAC vinylbenzyl trimethylammonium chloride
SO3 4-vinylbenzenesulfonic acid
IDA vinylbenzyliminodiacetic acid
BB base-bead (DVB/PS)

The sorbent of the present invention may be produced either in a one or a two step method using suspension polymerization or by a process in which beads absorb the monomers or a solution of monomers, or a process in which beads swell in the monomers or a solution of monomers. The method comprises providing at least one nitrogen-containing cyclic compound, a cross-linking agent, a solvent and a polymerisation initiator. The nitrogen containing cyclic compound may be conjugated or non-conjugated. In one embodiment the provided components are mixed into a monomer solution, and preferably purged with a noble gas in order to remove dissolved oxygen. The two stop method comprises providing a pre-formed bead prior to the polymerization step.

The solvent may be any organic solvent in which the reactants may be partly or fully dissolved. Examples of solvents are toluene, naphthalene, benzene, cyclohexane, acetonitrile, chloroform, dichloromethane, tetrahydrofuran, ethyl acetate dimethyl sulfoxide, dimethyl formamide and formic acid or mixtures thereof. The amount of solvent used may be in the range of 100 to 400 weight % in relation to the monomer mixture, preferably from 150 to 250 weight %. The monomer mixture is a mixture of the nitrogen containing cyclic compounds, other monomers and the cross-linking agent.

Suitable polymerization initiators may be any known to a person skilled in the art and could be for example different peroxides, various azo containing components or persulfates. Non-limiting examples can be benzyl peroxide, azoisobutylnitril (AIBN), 2,2"-azobis(2,4-dimethylvaleronitrile) or potassium persulfate. The amount of initiator is added in the range of 0.1 to 4.0 weight % with respect to the monomer mixture.

In one embodiment a pre-formed bead is provided where the bead is either polymeric or inorganic, and the bead may be porous. The pre-formed bead may have a size of 10 to 400 µm, preferably 30 to 90 µm. The pre-formed bead may be porous or non-porous. The weight ratio of pre-formed beads to monomer solution may be between 1:1 to 1:10, for example 1:1.5 or less, or 1:2 or less, or 1:3 or less, or 1:9 or more, or 1:7 or more. The monomer solution may be added all at once or in two or more portions.

In one embodiment a stabilizer is added and this is preferred especially when there is no pre-formed bead used, i.e. when the core portion of the sorbent comprises the same material as the outermost surface or another material partly based on nitrogen containing cyclic compounds. The function of the suspension stabilizer is to prevent coagulation of the droplets during polymerization. Suitable suspension stabilizers of this invention comprise water-soluble synthetic and natural polymers, e.g. poly(vinyl alcohol), partly saponified poly(vinyl acetate), methyl cellulose, hydroxyethyl cellulose or other cellulose derivatives, polyacrylic acid sodium salts, carboxymethyl cellulose sodium salt, polyvinyl pyrrolidone, and furthermore.

All the added components are then mixed for example by stirring or shaking and the mixture is allowed to polymerize. When a stabilizer is used a two phase system is usually formed and in order to obtain a sorbent of bead shape stirring is preferred during mixing, and preferably at a rate of 150 rpm or more, or 250 rpm or more, or 300 rpm or more. The polymerization may be performed at any suitable temperature depending on the solvent, initiator or monomers used.

In one embodiment the polymerization temperature is 20° C. or more, or 30° C. or more, or 50° C. or more, or 80° C. or more. The polymerization may continue for 1 hour or more, or 5 hours or more, or 12 hours or more, or 24 hours or more, or 36 hours or more. The polymerization may also be performed at two or more different temperature intervals, i.e. the polymerization may first be performed at for example 50° C. for 24 h and then at 70° C. for 12 h. In one embodiment the first temperature interval may be at 40-60° C. for 15-24 h, and the second temperature interval may be at 65-80° C. for 5-15 h.

The polymerization mixture may be left to cool down before isolating the obtained sorbent. Preferably the obtained sorbent is washed with one or more suitable solvents, for example methanol, ethanol, ethyl acetate, formic acid and acetonitrile, and preferably the sorbent is then dried. The drying may be done at an elevated temperature and/or at reduced pressure. The obtained sorbent may be particulate, for example spherical, and have a particle size of 20 to 500 µm, preferably 30 to 90 µm, and if the sorbent is porous the pore size is preferably in the range of 50 to 1000 Å, preferably 50 to 500 Å. In one embodiment the sorbent is non-porous.

When a pre-formed porous bead is used and the bead absorbs the monomers or the solution of monomers or swell in the monomers or the solution of monomers, the monomers, cross-linking agent and the initiator will be partly located in the porous system of the bead. The polymerization and the cross-linking of the monomers will then form a physically attached or anchored polymeric net around and inside the bead. In this way not only the outer surface of the bead may capture the polar component but also the pores.

The sorbent of the present invention may be in form of beads but may also be in the form of a monolith. Furthermore, the sorbent may be mixed with other sorbents or solvents in order to optimize the wanted separation effect. The present invention further relates to a solid phase extraction cartridge comprising the sorbent of the present invention, and it relates to a separation column comprising the sorbent.

The present invention further relates to the use of a sorbent having a core portion and an outermost portion, and wherein at least the outermost portion of the sorbent comprises a cross-linked polymer partly based on nitrogen containing cyclic compounds and wherein the core portion comprises the same material as the outermost portion or another material partly based on nitrogen containing cyclic compounds, for extracting polar compounds such as mycotoxins.

EXPERIMENTS

Example 1, Preparation of Sorbent Material Ex 1

Step 1: Preparation of Polymer Pre-Formed Beads

Styrene (100 mL), divinyl benzene 80% technical grade (100 mL) and 2,2'-azobis(2,4-dimethylvaleronitrile) (3.0 g) were dissolved in a mixture of benzyl alcohol (200 mL) and chloroform (150 mL) and the solution was added to a 0.5% solution of polyvinylalcohol (Celvol 523) in deionized water (1150 mL). The two-phase mixture was stirred with 300 rpm at 50° C. for 15 h. After cooling, the formed polymer beads were collected by sieving, washed with methanol on a glass filter and dried.

Step 2: Preparation of Composite Sorbent, Pre-Formed Bead and a Polymeric Outermost Portion A monomer solution consisting of 53.1 g 1-vinylimidazole, 2.8 g divinyl benzene 80% technical grade and 1.3 g 2,2'-azobis(2,4-dimethylvaleronitrile) dissolved in 130 g toluene was prepared. The monomer solution was purged with nitrogen to remove dissolved oxygen. 100 g of the pre-formed beads from Step 1 were placed in a vessel and 177.9 g of the monomer solution was added in three portions under continuous stirring. The vessel was shaken thoroughly until a free-flowing material was obtained and then flushed with nitrogen and placed in an ultrasonication bath for 30 min. The polymerization was carried out first at 50° C. for 24 h and then at 70° C. for 12 h. The material was taken out of the vessel and washed with methanol, ethyl acetate, formic acid, acetonitrile and methanol again, and dried.

Example 2, Preparation of Sorbent Material Ex 2

The material was prepared in the same way as the previous material except that 53.1 g 4-vinylpyridine was used instead of 1-vinylimidazole in the second step.

Example 3, Preparation of Sorbent Material Ex 3

51.3 g 1-Vinylimidazole, 184.8 g trimethylolpropane trimethacrylate and 5.6 g benzoyl peroxide 75% were dissolved in 284 g toluene and the solution was added to a 2% solution of polyvinylalcohol (Celvol 523) in deionized water (1000 mL). The two-phase mixture was stirred with 300 rpm at 80° C. for 20 h. After cooling, the formed polymer beads were collected by sieving, washed with methanol, ethyl acetate, formic acid, acetonitrile and methanol again, and dried.

Example 4, Preparation of Sorbent Material Ex 4

The material was prepared in the same way as in Example 3 except that 57.3 g 4-vinylpyridine is used instead of 1-vinylimidazole.

Example 5

Evaluation of the Material with Patulin and Comparison with Other Materials 60 mg of each material from Experiment 1-4 (denoted Ex 1-Ex 4) was packed in SPE cartridges. The following solutions were passed through the cartridges:
1 mL of methanol
1 mL of 10% acetonitrile in water
1 mL of patulin (typically 1000 ng/mL), dissolved in 10 mM ammonium acetate, pH 5 in water
1 mL of 10 mM ammonium acetate, pH 5 in water The same experiment was also carried out with SPE cartridges packed with 40 mg of three different materials commonly used to extract analytes from water samples. The materials were all of the HLB type and one was a neutral material (HLB), one a strong cation exchanger (HLB-SCX) and one strong anion exchanger (HLB-SAX).

Each experiment was carried out in duplicate. The mycotoxin content of all fractions was analyzed using LC-MS/MS and the results are shown in Table 1.

TABLE 1

Amounts of patulin eluted in the load step (sample in 10 mM ammonium acetate, pH 5 in water) and wash step (10 mM ammonium acetate, pH 5 in water)

| Resin | Load | Wash |
|---|---|---|
| Ex 1 | 0% | 0% |
| Ex 2 | 0% | 1% |
| Ex 3 | 0% | 0% |
| Ex 4 | 0% | 1% |
| HLB | 8% | 8% |
| HLB-SCX | 12% | 5% |
| HLB-SAX | 5% | 3% |

Ex 1, 2, 3 and 4 means sorbent material obtained in Example 1, 2, 3 and 4.

The results demonstrate that the resins of the invention were able to extract patulin completely from aqueous solution and retain it during a wash step while the resins of the HLB type failed to extract patulin completely and partially released extracted patulin during the wash step.

Resins of the HLB type are commonly used for the extraction of various analytes from aqueous samples with excellent results, however in the case of patulin their performance is deficient. The reason for this may be that patulin is much more polar than many other common analytes such as most pharmaceuticals and environmental contaminants. The resins of the invention may be useful also for the extraction of other polar compounds that are difficult to extract with the conventional materials. Some examples of resins of the HLB type are the Oasis family (Waters), Supel-Select family (Supelco), EVOLUTE® family (Biotage) and the Strata-X family (Phenomenex).

Example 6

Evaluation of the Material with a Suite of Mycotoxins and Comparison with Other Materials 60 mg of each material was packed in SPE cartridges. The following solutions were passed through the cartridges:
1 mL of methanol
1 mL of 10% acetonitrile in water.
1 mL of mycotoxins (typically 50-1000 ng/mL), dissolved in 10% acetonitrile in water
1 mL of 10 mM ammonium acetate, pH 6.7 in water
1 mL of 20% isopropyl alcohol in 10 mM ammonium acetate buffer, pH 6.7

The same experiment was also carried out with SPE cartridges packed with 40 mg of three different materials commonly used to extract analytes from water samples. The materials were all of the HLB type and one was a neutral material (HLB), one a strong cation exchanger (HLB-SCX) and one strong anion exchanger (HLB-SAX).

Each experiment was carried out in duplicate. The mycotoxin content of all fractions was analyzed using LC-MS/MS and the results are shown in Tables 2-4.

TABLE 2

Amount eluted in the load step (sample in 10% MeCN in aqueous solution)

| Resin | Aflatox B1 | Aflatox G1 | Ergocryp. | Ergocor. | Ochratox A | Fumonis B1 | ZON | CPZA |
|---|---|---|---|---|---|---|---|---|
| Ex 1 | 0% | 0% | 0% | 0% | 0% | 1% | 0% | 1% |
| Ex 2 | 0% | 0% | 0% | 0% | 0% | 0% | 0% | 0% |
| Ex 3 | 0% | 0% | 0% | 0% | 0% | 0% | 0% | 1% |
| Ex 4 | 0% | 0% | 0% | 0% | 0% | 1% | 0% | 0% |
| HLB | 0% | 1% | 0% | 0% | 0% | 0% | 0% | 0% |
| HLB-SCX | 0% | 1% | 0% | 0% | 0% | 0% | 0% | 0% |
| HLB-SAX | 0% | 1% | 45% | 54% | 0% | 0% | 0% | 0% |

Ergocryp. = Ergocryptine,
Ergocor. = Ergocornine,
Ochratox = Ochratoxin,
Fumonis = Fumonisin,
ZON = zearalenone,
CPZA = Cyclopiazonic acid
Ex 1, 2, 3 and 4 means sorbent material obtained in Example 1, 2, 3 and 4.

TABLE 3

Amount eluted in the 1st wash step (10 mM ammonium acetate buffer, pH 6.7 in water)

| Resin | Aflatox B1 | Aflatox G1 | Ergocryp. | Ergocor. | Ochratox A | Fumonis B1 | ZON | CPZA |
|---|---|---|---|---|---|---|---|---|
| Ex 1 | 0% | 0% | 0% | 0% | 0% | 1% | 0% | 1% |
| Ex 2 | 0% | 0% | 0% | 0% | 0% | 1% | 0% | 0% |
| Ex 3 | 0% | 0% | 0% | 0% | 0% | 1% | 0% | 1% |
| Ex 4 | 0% | 0% | 0% | 0% | 0% | 2% | 0% | 1% |
| HLB | 0% | 0% | 0% | 0% | 0% | 0% | 0% | 0% |
| HLB-SCX | 0% | 0% | 0% | 0% | 0% | 0% | 0% | 0% |
| HLB-SAX | 0% | 0% | 0% | 0% | 0% | 0% | 0% | 0% |

Ergocryp. = Ergocryptine,
Ergocor. = Ergocornine,
Ochratox = Ochratoxin,
Fumonis = Fumonisin,
ZON = zearalenone,
CPZA = Cyclopiazonic acid
Ex 1, 2, 3 and 4 means sorbent material obtained in Example 1, 2, 3 and 4.

TABLE 4

Amount eluted in the 2nd wash step (20% isopropyl alcohol in buffer)

| Resin | Aflatoxin B1 | Aflatoxin G1 | Ergocryp | Ergocor | Ochratox A | Fumonis B1 | ZON | CPZA |
|---|---|---|---|---|---|---|---|---|
| Ex 1 | 0% | 1% | 0% | 0% | 0% | 0% | 0% | 1% |
| Ex 2 | 0% | 1% | 0% | 0% | 0% | 23% | 0% | 0% |
| Ex 3 | 0% | 0% | 0% | 0% | 0% | 17% | 0% | 0% |
| Ex 4 | 0% | 0% | 0% | 0% | 0% | 43% | 0% | 1% |
| HLB | 28% | 72% | 69% | 23% | 79% | 55% | 11% | 17% |
| HLB-SCX | 1% | 9% | 0% | 0% | 32% | 117% | 0% | 0% |
| HLB-SAX | 2% | 11% | 1% | 1% | 0% | 0% | 0% | 0% |

Ergocryp. = Ergocryptine,
Ergocor. = Ergocornine,
Ochratox = Ochratoxin,
Fumonis = Fumonisin,
ZON = zearalenone,
CPZA = Cyclopiazonic acid
Ex 1, 2, 3 and 4 means sorbent material obtained in Example 1, 2, 3 and 4.

All resins except HLB-SAX were able to extract the mycotoxins completely from aqueous solution and retain them during a wash step but only the resins of the invention were able to retain the mycotoxins aflatoxin, ergot alkaloids, ochratoxin A and ZON in 20% isopropyl alcohol in water. This enables the use of stronger wash solutions leading to cleaner extracts and more reliable analysis of the mycotoxins.

Example 7, Extraction of Mycotoxins from Flour

Column configuration: Sorbent according to Example 1 60 mg/3 mL

Extraction Procedure 5 g of whole wheat flour was weighed and mixed with 20 mL of a 50% acetonitrile in water solution. The slurry was extracted for 30 minutes on a shaking table. The extracted sample was transferred to a 50 mL centrifuge tube and centrifuged at 3000 g for 10 minutes to remove solids. A fraction of the supernatant (8 mL) was transferred to a new centrifuge tube and diluted with water (32 mL) to make the acetonitrile content 10%. The solution was centrifuged again for 10 minutes at 3000 g.

Sample Preparation Procedure

1. Conditioning—2 mL of acetonitrile was applied and was allowed to flow through the sorbent bed. 2 mL of water was added, and was allowed to flow through the bed.
2. Load—3 mL of sample (centrifuged and diluted to an acetonitrile content of 10%) was added. The sample was allowed to flow through the sorbent bed slowly (preferably gravity only).
3. Wash 1—3 mL of 10 mM ammonium acetate, pH 6.7, was added.
4. Wash 2—3 mL of 10% acetonitrile in 10 mM ammonium acetate, pH 6.7, was applied. Air was pulled through the column for 10-30 seconds.
5. Elution 1—2 mL of 0.1% formic acid in acetonitrile was applied
6. Elution 2—2 mL of methanol was applied
7. Evaporation—The solvent was evaporated at 30° C. for 40 min in a TurboVap at 1.5 bar and reconstituted in 1 mL of reconstitution solution (20% acetonitrile in 5 mM ammonium carbonate, pH 9)

Results

The results of the extraction using the method and material of the present invention was analysed using HPLC and LC-MS.

High Mycotoxin Concentration (200 ng Mycotoxin/g Flour)

The samples were extracted and prepared as described in sections above. Spiking the extracts with mycotoxins for a concentration of 10 ng/mL diluted extract (correspond to 200 ng mycotoxin/g flour) gave good signals ensuring more accurate data. The resulting data are presented in Table 5.

TABLE 5

Recoveries after sample treatment, extract spiked at a level 10 ng Mycotoxin/mL diluted extract (correspond to a level of 200 ng Mycotoxin/g flour) prior to SPE. Compensated for ion suppression effects, i.e. compared to blank extracts spiked with the corresponding amounts of mycotoxins.

| Compound | Elution 1 | Elution 2 | Total recovery (%) |
| --- | --- | --- | --- |
| Aflatoxin B1 | 101 | 0 | 102 |
| Aflatoxin G1 | 96 | 0 | 96 |
| Ergotamine | 101 | 1 | 101 |
| Ergocryptine | 99 | 1 | 100 |
| Ergocornine | 99 | 1 | 100 |
| Ochratoxin A | 93 | 2 | 95 |
| Fumonisin B1 | 7 | 84 | 91 |
| Zearelenone | 95 | 1 | 96 |
| Cyclopiazonic acid | 100 | 0 | 100 |

As can be seen from the results, recoveries were in the 91-102% range. All components except fumonisin elute with 2 mL of 1% formic acid in acetonitrile. Methanol was required to elute fumonisin from the sorbent. Ion suppression/enhancement effects were compensated for by comparing the simulated samples to blank extracts spiked with mycotoxins.

Ion suppression/enhancement was monitored by spiking blank flour extracts (treated as above) after SPE procedure, but prior to evaporation and comparing the peak area with that obtained from mycotoxins in mobile phase. Results are presented in Table 6.

TABLE 6

Ion suppression after sample treatment, blank extract spiked at a level 10 ng Mycotoxin/mL diluted extract (correspond to a level of 200 ng Mycotoxin/g flour) after SPE compared with mycotoxins in mobile phase (no matrix components)

| Compound | Elution 1 | Elution 2 |
| --- | --- | --- |
| Aflatoxin B1 | −14% | −12% |
| Aflatoxin G1 | −23% | −31% |
| Ergotamine | −17% | −8% |
| Ergocryptine | −11% | −19% |
| Ergocornine | −9% | −10% |
| Ochratoxin A | 11% | 12% |
| Fumonisin B1 | −43% | 67% |
| Zearelenone | −5% | −4% |
| Cyclopiazonic acid | −67% | −54% |

For all components except fumonisin and cyclopiazonic acid the ion suppression is between −23% to +11% (focusing the discussion to elution 1 fractions since all components except fumonisin were eluted in elution 1) which can be considered satisfactorily. For fumonisin there was significant ion enhancement in elution 2 (which was the fraction in which fumonisin elute).

Low Mycotoxin Concentration (20 ng Mycotoxin/g Flour)

The samples were extracted and prepared as described in sections above. The extracts were spiked with mycotoxins for a concentration of 1 ng/mL diluted extract (correspond to 20 ng mycotoxin/g flour) representing more realistic levels of mycotoxins. The resulting data are presented in Table 7.

TABLE 7

Recoveries after sample treatment, extract spiked at a level 1 ng Mycotoxin/mL diluted extract (correspond to a level of 20 ng Mycotoxin/g flour) prior to SPE. Compensated for ion suppression effects, i.e. compared to blank extracts spiked with the corresponding amounts of mycotoxins.

| Compound | Elution 1 | Elution 2 | Total recovery (%) |
| --- | --- | --- | --- |
| Aflatoxin B1 | 99 | 2 | 101 |
| Aflatoxin G1 | 109 | 1 | 110 |
| Ergotamine | 106 | 1 | 108 |
| Ergocryptine | 93 | 2 | 95 |
| Ergocornine | 95 | 1 | 97 |
| Ochratoxin A | 80 | 6 | 86 |
| Fumonisin B1 | 1 | 72 | 73 |
| Zearelenone | 97 | 0 | 98 |
| Cyclopiazonic acid | 123 | 1 | 124 |

As can be seen from the results, recoveries are in the 73-124% range. All components except fumonisin were eluted with 2 mL of 1% formic acid in acetonitrile. Ion suppression/enhancement effects were compensated for by comparing the simulated samples to blank extracts spiked with mycotoxins after SPE.

Ion suppression/enhancement was monitored by spiking blank flour extracts (treated as above) after SPE procedure, but prior to evaporation and comparing the peak area with that obtain from mycotoxins in mobile phase. The results are presented in Table 8.

TABLE 8

Ion suppression after sample treatment, blank extract spiked at a level
of 1 and 10 ng Mycotoxin/mL diluted extract (correspond to a level of 20
and 200 ng Mycotoxin/g flour) after SPE compared with mycotoxins
in mobile phase (no matrix components)

|  | Spiked to 1 ng/mL | | Spiked to 10 ng/mL | |
| --- | --- | --- | --- | --- |
| Compound | Elution 1 | Elution 2 | Elution 1 | Elution 2 |
| Aflatoxin B1 | −19% | −21% | −14% | −12% |
| Aflatoxin G1 | −15% | −27% | −23% | −31% |
| Ergotamine | −5% | −27% | −17% | −8% |
| Ergocryptine | −16% | −39% | −11% | −19% |
| Ergocornine | −9% | −18% | −9% | −10% |
| Ochratoxin A | 1% | −6% | 11% | 12% |
| Fumonisin B1 | −22% | −22% | −43% | 67% |
| Zearelenone | 2% | −6% | −5% | −4% |
| Cyclopiazonic acid | −21% | −9% | −67% | −54% |

For all components except fumonisin and cyclopiazonic acid the ion suppression was between −23% to +11% (focusing the discussion to elution 1 fractions since all components except fumonisin were eluted in elution 1) which can be considered satisfactorily. For fumonisin there was significant variation in the results, ion suppression of 22% at low level and ion enhancement of 67% at high level. Similar effects were seen for cyclopiazonic acid.

Example 8—Extraction Mycotoxins from Wheat, Maize or Barley

Column configuration: Sorbent according to Example 1 60 mg/3 mL
Extraction Procedure:
The sample (wheat, maize, barley, 50 g) was grind with a grinder on the coarsest setting. The grind sample was stored in a sealed container at room temperature until required. The sample was extracted by mixing the ground whole grain (or flour) sample (5 g) with 50% acetonitrile (aq.) (20 mL) and placed on a shaking table for 30 minutes. The extract was transferred to a 50 mL centrifuge tube and centrifuged at 3000 g for 10 minutes. The supernatant (8 mL), was transferred to a new 50 mL centrifuge tube and diluted with water (32 mL). The diluted extract was centrifuged at 3000 g for a further 10 minutes.

Sample Preparation Procedure
1. Conditioning: Flow rate used was of 1 mL min$^{-1}$ throughout. The column was conditioned with acetonitrile (2×1 mL) and equilibrated with water (2 mL).
2. Sample loading: The pre-treated sample (3 mL) was loaded onto the column at a maximum flow rate of 1 mL min$^{-1}$.
3. Wash 1: The column was washed with water (3 mL).
4. Wash 2: The column was washed with 10% acetonitrile (3 mL).
5. Drying: The column was dried for 30 seconds at maximum vacuum, 2 bar/29 psi
6. Elution 1: Eluted with 0.1% formic acid in acetonitrile (2 mL).
7. Elution 2: Eluted with methanol (2 mL)
8. Post elution: The eluent was dried in a stream of air or nitrogen using a SPE Dry (35° C., 20 to 40 L min$^{-1}$) or TurboVap LV (1.5 bar at 35° C. for 40 min). Reconstituted in 0.1% acetic acid in 20% acetonitrile:methanol (1 mL, 1:1, v/v). Syringe-filter using a 0.2 μm PTFE membrane prior to analysis.

Results
The results of the extraction using the method and material of the present invention was analysed using HPLC and LC-MS.

All analytes extracted using the material (ISOLUTE®) and method of the present invention achieved the limits of quantities and recovery required by the current European standards for mycotoxin analysis as shown in tables 9, 10 and 11.

TABLE 9

Analyte recovery and limit of quantitation data for a range of mycotoxins
from wheat grain using the ISOLUTE ® Myco protocol

| Analyte | | LOQ/μg kg$^{-1}$ | | % RSD$_r$ | | Recovery % | |
| --- | --- | --- | --- | --- | --- | --- | --- |
| Wheat | r$^2$ | Target | Actual | Target | Actual | Target | Actual |
| aflatoxin B1 | 0.9994 | 2 | 0.67 | 40 | 3.0 | 50 to 120 | 96 |
| aflatoxin B2 | 0.9995 | 2 | 0.67 | 40 | 5.6 | 50 to 120 | 102 |
| aflatoxin G1 | 0.9990 | 2 | 0.67 | 40 | 3.7 | 50 to 120 | 99 |
| aflatoxin G2 | 0.9998 | 2 | 1.33 | 40 | 3.3 | 70 to 110 | 110 |
| ochratoxin A | 0.9995 | 3 | 1.33 | 40 | 5.9 | 70 to 110 | 88 |
| T-2 toxin | 0.9996 | 50 | 13.3 | 40 | 3.8 | 60 to 130 | 102 |
| HT-2 toxin | 0.9987 | 100 | 26.7 | 40 | 19.0 | 60 to 130 | 106 |
| fumonisin B1 | 0.9997 | 1000 | 26.7 | 30 | 2.8 | 60 to 120 | 100 |
| zearalenone | 0.9996 | 50 | 26.7 | 40 | 1.8 | 60 to 120 | 73 |
| ergocornine | 0.9997 | N/A | 13.3 | N/A | 5.9 | N/A | 96 |
| ergocryptine | 0.9996 | N/A | 13.3 | N/A | 4.2 | N/A | 76 |

TABLE 10

Analyte recovery and limit of quantitation data for a range of mycotoxins
from maize grain using the ISOLUTE ® Myco protocol

| Analyte | | LOQ/μg kg$^{-1}$ | | % RSD$_r$ | | Recovery % | |
| --- | --- | --- | --- | --- | --- | --- | --- |
| Maize | r$^2$ | Target | Actual | Target | Actual | Target | Actual |
| aflatoxin B1 | 0.9994 | 2 | 0.67 | 40 | 4.2 | 50 to 120 | 94 |
| aflatoxin B2 | 0.9988 | 2 | 0.67 | 40 | 2.6 | 50 to 120 | 96 |
| aflatoxin G1 | 0.9995 | 2 | 0.67 | 40 | 3.3 | 50 to 120 | 97 |

TABLE 10-continued

Analyte recovery and limit of quantitation data for a range of mycotoxins from maize grain using the ISOLUTE ® Myco protocol

| Analyte | | LOQ/µg kg$^{-1}$ | | % RSD$_r$ | | Recovery % | |
|---|---|---|---|---|---|---|---|
| Maize | r$^2$ | Target | Actual | Target | Actual | Target | Actual |
| aflatoxin G2 | 0.9993 | 2 | 1.33 | 40 | 2.4 | 70 to 110 | 95 |
| ochratoxin A | 0.9997 | 3 | 1.33 | 40 | 3.8 | 70 to 110 | 72 |
| T-2 toxin | 0.9992 | 50 | 13.3 | 40 | 2.4 | 60 to 130 | 99 |
| HT-2 toxin | 0.9989 | 100 | 13.3 | 40 | 4.5 | 60 to 130 | 97 |
| fumonisin B1 | 0.9993 | 1000 | 267 | 30 | 2.6 | 60 to 120 | 100 |
| zearalenone | 0.9995 | 50 | 26.7 | 40 | 2.8 | 60 to 120 | 71 |
| ergocornine | 0.9995 | N/A | 13.3 | N/A | 2.0 | N/A | 78 |
| ergocryptine | 0.9995 | N/A | 13.3 | N/A | 1.1 | N/A | 77 |

TABLE 11

Analyte recovery and limit of quantitation data for a range of mycotoxins from barley grain using the ISOLUTE Myco protocol

| Analyte | | LOQ/µg kg$^{-1}$ | | % RSD$_r$ | | Recovery % | |
|---|---|---|---|---|---|---|---|
| Barley | r$^2$ | Target | Actual | Target | Actual | Target | Actual |
| aflatoxin B1 | 0.9996 | 2 | 1.33 | 40 | 5.0 | 50 to 120 | 100 |
| aflatoxin B2 | 0.9995 | 2 | 0.67 | 40 | 4.3 | 50 to 120 | 99 |
| aflatoxin G1 | 0.9992 | 2 | 1.33 | 40 | 2.1 | 50 to 120 | 99 |
| aflatoxin G2 | 0.9989 | 2 | 1.33 | 40 | 3.4 | 70 to 110 | 98 |
| ochratoxin A | 0.9990 | 3 | 2.00 | 40 | 4.5 | 70 to 110 | 96 |
| T-2 toxin | 0.9981 | 50 | 13.3 | 40 | 8.5 | 60 to 130 | 96 |
| HT-2 toxin | 0.9988 | 100 | 20.0 | 40 | 8.8 | 60 to 130 | 100 |
| fumonisin B1 | 0.9995 | 1000 | 13.3 | 30 | 2.0 | 60 to 120 | 84 |
| zearalenone | 0.9995 | 50 | 26.7 | 40 | 8.7 | 60 to 120 | 96 |
| ergocornine | 0.9996 | N/A | 13.3 | N/A | 2.2 | N/A | 82 |
| ergocryptine | 0.9997 | N/A | 13.3 | N/A | 2.5 | N/A | 85 |

Example 9—Extraction of Mycotoxins from Brazil Nut and Peanut (Groundnut

Column configuration: Sorbent of Example 1 60 mg/3 mL (Tabless)

Extraction Procedure:

The sample (peanut, brazil nut, 50 g) was grind and the sample stored in a sealed container at 2-8° C. until required. The grind whole nut sample (5 g) was mixed with 80% acetonitrile (aq) (20 mL) and placed on a shaking table for 30 minutes. The extract was transferred to a 50 mL centrifuge tube and centrifuged at 3000 g for 10 minutes. The supernatant (4 mL) was transferred to a new 50 mL centrifuged tube and dilute with water (28 mL). The diluted extract was centrifuged at 3000 g for a further 10 minutes.

Sample Preparation Procedure

Flow rates of 1 mL min$^{-1}$ was used throughout

1. Conditioning The column was conditioned with acetonitrile (2×1 mL) and equilibrated with 10 mM ammonium acetate (2 mL).
2. Loading Pre-treated sample (3 mL) was loaded onto the column at a maximum flow rate of 1 mL min$^{-1}$.
3. Wash 1 The column was washed with 10 mM ammonium acetate (3 mL).
4. Wash 2 The column was washed with 10 mM ammonium acetate in 10% acetonitrile (3 mL).
5. Drying The column was dried for 30 seconds at maximum vacuum, 2 bar/29 psi
6. Elution 1 Eluted with 0.1% formic acid in acetonitrile (2 mL).
7. Elution 2 Eluted with 0.1% formic acid in methanol (2 mL)
8. Post elution The eluent was dried in a stream of air or nitrogen using a SPE Dry (35° C., 20 to 40 L min$^{-1}$) or TurboVap LV (1.5 bar at 35° C. for 40 min). Reconstituted in 0.1% acetic acid in 20% acetonitrile:methanol (1 mL, 1:1, v/v) and take up in a syringe-filter with a 0.2 µm PTFE membrane prior to analysis.

Results

The results of the extraction using the method and material of the present invention were analysed using HPLC and LC-MS.

All analytes extracted using the ISOLUTE® Myco protocol (the material and method according to the present invention) achieved the limits of quantities and recovery required by the current European standards for mycotoxin analysis as shown in tables 12 and 13.

TABLE 12

Analyte recovery and limit of quantitation data for a range of mycotoxins from brazil nut using the ISOLUTE ® Myco protocol

| Analyte Brazil nut | $r^2$ | LOQ/µg kg$^{-1}$ Target | Actual | % RSD$_r$ Target | Actual | Recovery % Target | Actual |
|---|---|---|---|---|---|---|---|
| aflatoxin B1 | 0.9982 | 2 | 0.67 | 40 | 2.4 | 50 to 120 | 106 |
| aflatoxin B2 | 0.9978 | 2 | 0.67 | 40 | 4.9 | 50 to 120 | 103 |
| aflatoxin G1 | 0.9978 | 2 | 0.67 | 40 | 9.4 | 50 to 120 | 102 |
| aflatoxin G2 | 0.9982 | 2 | 0.67 | 40 | 7.4 | 70 to 110 | 114 |
| ochratoxin A | 0.9991 | 3 | 0.67 | 40 | 1.6 | 70 to 110 | 93 |

TABLE 13

Analyte recovery and limit of quantitation data for a range of mycotoxins from peanut using the ISOLUTE ® Myco protocol

| Analyte Peanut | $r^2$ | LOQ/µg kg$^{-1}$ Target | Actual | % RSD$_r$ Target | Actual | Recovery % Target | Actual |
|---|---|---|---|---|---|---|---|
| aflatoxin B1 | 0.9960 | 2 | 1.33 | 40 | 8.5 | 50 to 120 | 102 |
| aflatoxin B2 | 0.9939 | 2 | 1.33 | 40 | 8.4 | 50 to 120 | 110 |
| aflatoxin G1 | 0.9973 | 2 | 0.67 | 40 | 3.4 | 50 to 120 | 108 |
| aflatoxin G2 | 0.9993 | 2 | 0.67 | 40 | 8.9 | 70 to 110 | 114 |
| ochratoxin A | 0.9993 | 3 | 0.67 | 40 | 6.7 | 70 to 110 | 93 |

Example 10—Extraction of Aflatoxin M1 from Infant Formula Using ISOLUTE® Myco Prior to LC-MS/MS Analysis This example describes a Solid Phase Extraction (SPE) protocol for the extraction of aflatoxin M1 (AM 1) internally standardized with aflatoxin B2 (AB2) from infant formula using ISOLUTE Myco with LC-MS/MS.

Analytes
  Aflatoxin M1, aflatoxin B2 (internal standard).
Sample Preparation Procedure
Column configuration: ISOLUTE® Myco 60 mg/3 mL (Tabless), part number 150-0006-BG
Sample Pre-Treatment:
  1. Sample processing: reconstitute the infant formula according to the manufacturer's recommendations using 1% formic acid (aq) as the solvent. Add a small volume of AB2 at an appropriate concentration (e.g. 18 µL×100 ng mL$^{-1}$ AB2/36 mL formula=50 ng LA
  2. Extraction: shake the reconstituted formula vigorously by hand for 30 seconds. Place the sample tube in an ultrasonic water bath and sonicate for 20 minutes. Centrifuge the sample tube at 4000 g for 10 minutes.
  3. Work-up: Spoon off and discard the upper cream layer.
Solid Phase Extraction
Flow rate: 1 mL min$^{-1}$
Condition: Condition the column with acetonitrile (2 mL).
Equilibration: Equilibrate column with water (2 mL).
Sample loading: Load pre-treated sample (5 mL) onto the column at a maximum flow rate of 1 mL min$^{-1}$ (gravity load is recommended).
Interference wash 1: Wash the column with water (5 mL).
Interference wash 2: Wash the column with 10% acetonitrile (5 mL).
Drying: Dry the column for 5 minutes at maximum vacuum, 2 bar/29 psi.
Interference wash 3: Wash the column with hexane (5 mL).
Drying: Dry the column for 5 minutes at maximum vacuum, 2 bar/29 psi.
Elution: Elute with 0.1% formic acid in acetonitrile (2 mL)
Post elution: The eluate is dried in a stream of air or nitrogen using a SPE Dry (35° C., 20 to 40 L min$^{-1}$) or TurboVap LV (1.5 bar at 35° C. for 40 min). Reconstitute in 0.1% acetic acid in 20% acetonitrile:mthanol (1 mL, 1:1, v/v). Syringe-filter using a 0.2 µm PTFE membrane prior to analysis.
HPLC Conditions
Instrument: Shimadzu Nexera UHPLC (Shimadzu Europe Gmbh)
Column: Kinetex XB-C18 50×2.1 mm 2.6 µm dp (Phenomenex, Macclesfield UK)
Mobile Phase:
A: 1 mM ammonium acetate, 0.5% acetic acid
B: 1 mM ammonium acetate, 0.5% acetic acid in 95% methanol (aq)
Flow rate: 0.45 mL min$^{-1}$
Injection: 20 µL
Gradient: Initial 20% B, hold 1.0 min
linear ramp to 73% B in 6 min
linear ramp to 100% B in 0.2 min, hold 2.3 min
linear ramp to initial conditions in 0.2 min
hold 2.3 min, total run time 10.0 min
Column temperature: 40° C.
Sample temperature: 15° C.

TABLE 14

Typical retention times for AM1 and AB2 using the LC-MS/MS method described.

| Compound | Retention time (min) |
|---|---|
| aflatoxin M1 | 3.4 |
| aflatoxin B2 | 3.8 |

MS Conditions

Ions were selected in order to achieve maximum sensitivity, and the MS was operated in positive polarity mode, using multiple reaction monitoring.
Instrument: AB Sciex Triple Quad 5500 (Warrington, UK)
Source: Turbo-V ESI
Desolvation temp.: 500° C.
Curtain gas: 30 psi
Spray voltage: +5.0 kV
Gas 1:60 psi Gas 2:60 psi
Collision gas: 7 psi

TABLE 15

Positive Ion Mode - MRM Parameters

| MRM transition | RT Compound ID | DP, V | EP, V | CE, V | CXP, V |
|---|---|---|---|---|---|
| 329.0 > 273.3 | 3.4 aflatoxin M1 1 | 80 | 10 | 32 | 12 |
| 329.0 > 229.2 | 3.4 aflatoxin M1 2 | 80 | 10 | 52 | 12 |
| 329.0 > 301.1 | 3.4 aflatoxin M1 3 | 80 | 10 | 26 | 12 |
| 315.1 > 287.0 | 3.8 aflatoxin B2 1 | 100 | 10 | 35 | 12 |
| 315.1 > 259.1 | 3.8 aflatoxin B2 2 | 100 | 10 | 40 | 12 |
| 315.1 > 243.1 | 3.8 aflatoxin B2 3 | 100 | 10 | 51 | 12 |

MRM detection window 60 s/target scan time 0.1 s/settling time 50 ms/scan pause 5 ms Validation Criteria Method linearity was determined using internally standardized matrix-matched calibrants in six replicates over eight levels; the ranges are shown below.

| Analytes | Working Range, ng $L^{-1}$ (fg $\mu L^{-1}$ on-column) |
|---|---|
| aflatoxin M1 | 2 to 100 (10 to 500) |
| aflatoxin B2 (internal standard) | 40 (200) |

LOQ was determined from the lowest matrix-matched standard meeting EU repeatability and recovery criteria.

Repeatability (% $RSD_r$) was determined from single acquisitions of 4 SPE replicates of a single sample extraction. The RSDs generated gave close agreement when a single sample was extracted and processed using ISOLUTE Myco from three separate sorbent batches.

Recovery was determined as a % of ISOLUTE Myco extract spike before sample prep to spike after close to the analytical LOQ.

Results

Figure 3:
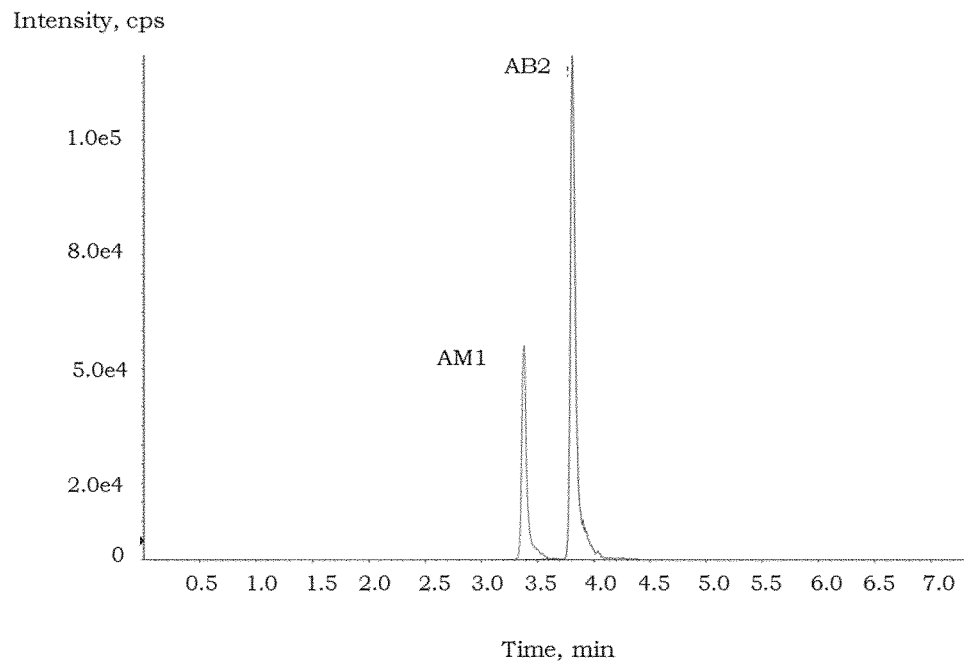
FIG. 3, shows extracted ion chromatograms in positive ion mode using ISOLUTE Myco protocol at 50 ng $L^{-1}$ (aflatoxin M1 and aflatoxins B2) from reconstituted infant formula.

The extracted ion chromatograms in FIG. 3 demonstrates chromatography at 50 ng $L^{-1}$ (aflatoxin M1, aflatoxin B2) from a spiked extraction of 6 g dried infant formula reconstituted with 36 mL 1% formic acid (aq). Good linearity was achieved for aflatoxin M1 as demonstrated in the example chart shown in FIG. 4.

Figure 4:
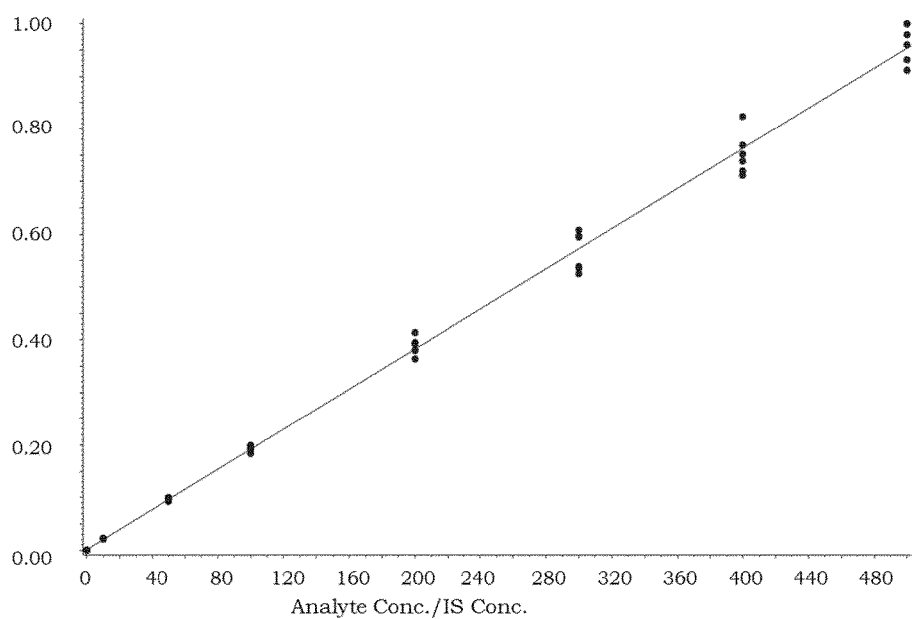
FIG. 4, shows internally standardized calibration curve for aflatoxin M1 from reconstituted infant formula using the ISOLUTE Myco protocol from 2-100 ng $L^{-1}$ (aflatoxin B2 at 40 ng $L^{-1}$).

FIG. 4 shows internally standardized calibration curve for aflatoxin M1 from reconstituted infant formula using the ISOLUTE Myco protocol from 2-100 ng $L^{-1}$ (aflatoxin B2 at 40 ng $L^{-1}$)

Aflatoxin M1 extracted using the ISOLUTE Myco protocol achieved the limits of quantities and recovery required by the current European standards for mycotoxin analysis as shown in table 16.

TABLE 16

Analyte recovery and limit of quantitation data for aflatoxin M1 from reconstituted infant formula using the ISOLUTE Myco protocol

| | | LOQ/ng $kg^{-1}$ | | % $RSD_r$ | | Recovery % | |
|---|---|---|---|---|---|---|---|
| Analyte | $r^2$ | Target | Actual | Target | Actual | Target | Actual |
| aflatoxin M1 | 0.9977 | 25 | 2 | 20 | 6.4 | 70 to 110 | 90 |

Example 11—Extraction of Multiple Mycotoxins from Animal Feed Using ISOLUTE® Myco Prior to LC-MS/MS Analysis This example describes a Solid Phase Extraction (SPE) protocol for the extraction of a range of mycotoxins from animal feed using ISOLUTE Myco with LC-MS/MS.

Analytes

Aflatoxin B1, ochratoxin A, fumonisin B1, zearalenone, T-2 mycotoxin, HT-2 mycotoxin, deoxynivalenol.

Sample Preparation Procedure

Column configuration: ISOLUTE® Myco 60 mg/3 mL (Tabless), part number 150-0006-BG Sample pre-treatment:
  A) Mycotoxin Classes Excluding Type B Tricothecenes
  4. Sample processing: Grind the sample (50 g) with a burr-grinder or equivalent device. Store ground sample in a sealed container at room temperature until required.
  5. Extraction: Mix the ground sample (5 g) with 4% formic acid (aq) (10 mL) and shake vigorously by hand for 30 seconds. Add acetone (30 mL) and shake vigorously by hand for 30 seconds. Place the sample pre-treatment tube on a shaking table for 30 minutes. Transfer the extract to a 50 mL centrifuge tube and centrifuge at 4000 g for 10 minutes.
  6. Dilution: Take the supernatant (6 mL), transfer to a new 50 mL centrifuge tube and dilute with water (39 mL). Centrifuge diluted extract at 4000 g for a further 10 minutes.
  B) Type B Trichothecene Mycotoxins
  1. Sample processing: Grind the sample (50 g) with a burr-grinder or equivalent device. Store ground sample in a sealed container at room temperature until required.
  2. Extraction: Mix the ground sample (5 g) with 1% formic acid (aq) (40 mL) and shake vigorously by hand for 30 seconds. Place the sample pre-treatment tube on a shaking table for 30 minutes. Transfer the extract to a 50 mL centrifuge tube and centrifuge at 4000 g for 10 minutes.
  3. Dilution: Take the supernatant (6 mL), transfer to a new 50 mL centrifuge tube and dilute with water (39 mL). Centrifuge diluted extract at 4000 g for a further 10 minutes.

Solid Phase Extraction

Flow rate: 1 mL min$^{-1}$

A) Mycotoxin Classes Excluding Type B Tricothecenes

As in Example 10 but no interference wash after drying.

B) Type B Trichothecene Mycotoxins

As in A) but only one interference wash with water (3 mL).

HPLC Conditions

As in Example 10.

TABLE 17

Typical retention times for a range of mycotoxins using the LC-MS/MS method described.

| Compound | Retention time (min) |
|---|---|
| aflatoxin G2 | 3.3 |
| aflatoxin G1 | 3.6 |
| aflatoxin B2 | 3.9 |
| aflatoxin B1 | 4.1 |
| ochratoxin A | 6.1 |

MS Conditions

Ions were selected in order to achieve maximum sensitivity, and the MS was operated in dual polarity (+ve/−ve switching) mode, using multiple reaction monitoring. Instrument set up see Example 9 (spray voltage: +5.0 kV/−4.5 kV)

TABLE 18

Negative Ion Mode - MRM Parameters

| MRM transition | RT | Compound ID | DP, V | EP, V | CE, V | CXP, V |
|---|---|---|---|---|---|---|
| 355.1 > 59.0 | 0.7 | deoxynivalenol 1 | −50 | −10 | −45 | −15 |
| 335.1 > 295.1 | 0.7 | deoxynivalenol 2 | −50 | −10 | −13 | −15 |
| 335.1 > 265.1 | 0.7 | deoxynivalenol 3 | −50 | −10 | −20 | −15 |
| 720.2 > 157 | 5.4 | fumonisin B 1 | −160 | −12 | −45 | −15 |
| 720.2 > 562.3 | 5.4 | fumonisin B1 2 | −160 | −12 | −36 | −15 |
| 317.2 > 131 | 5.9 | zearalenone 1 | −40 | −4 | −38 | −15 |
| 317.2 > 175 | 5.9 | zearalenone 2 | −40 | −4 | −30 | −15 |
| 317.2 > 255.1 | 5.9 | zearalenone 3 | −40 | −4 | −20 | −15 |

MRM detection window 60 s/target scan time 0.1 s/settling time 50 ms/scan pause 5 ms Validation Criteria Method linearity was determined using matrix-matched calibration standards in six replicates over eight levels; the ranges are shown below.

| Analytes | Working Range, μg kg$^{-1}$ (pg μL$^{-1}$ on-column) |
|---|---|
| aflatoxin B1, ochratoxin A, T-2 toxin | 0.4 to 40.0 (0.02 to 2.0) |
| fumonisin B1, zearalenone, HT-2 toxin | 40 to 4000 (2 to 200) |
| deoxynivalenol | 40 to 4000 (2 to 200) |

LOQ was determined from the lowest matrix-matched standard meeting EU repeatability and recovery criteria. Where no criteria were specified the LOQ were estimated by correlation to similar analytes.

Repeatability (% RSD$_r$) was determined from single acquisitions of 5 SPE replicates of a single sample extraction. The RSDs generated gave close agreement when a single sample was extracted and processed using ISOLUTE Myco from three separate sorbent batches.

Recovery was determined as a % of ISOLUTE Myco extract spike before sample prep to spike after close to the analytical LOQ.

Results

Figure 8:
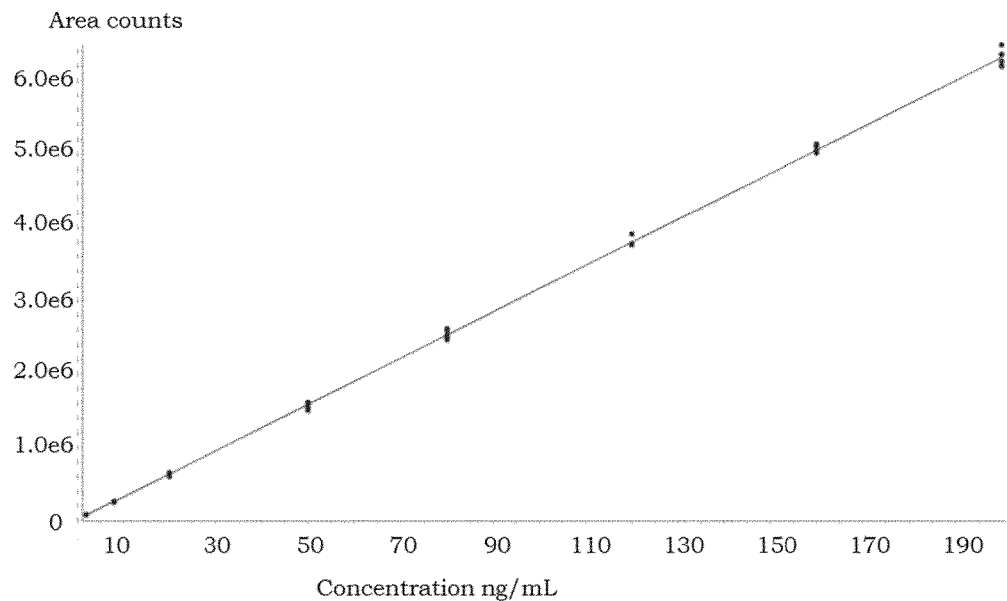

The extracted ion chromatograms in FIGS. 5 and 6 demonstrate chromatography at 5 μg kg$^{-1}$ (aflatoxin B1, ochratoxin A and T-2 toxin) and 100 μg kg$^{-1}$ for all other analytes from a spiked extraction of 5 g ground feed substrate. Good linearity was achieved for all analytes in all the different matrices as demonstrated in the example charts shown in FIGS. 7 and 8.

The majority of analytes extracted using the ISOLUTE Myco protocol achieved the limits of quantities and recovery required by the current European standards for mycotoxin analysis as shown in tables 19 and 20. Deoxynivalenol recovery from soya was lower than required, additional work is being undertaken to increase recovery of this analyte.

TABLE 19

Analyte recovery and limit of quantitation data for a range of mycotoxins from ground soya using the ISOLUTE Myco protocol

| Analyte Soya | r$^2$ | LOQ/μg kg$^{-1}$ Target | Actual | % RSD$_r$ Target | Actual | Recovery % Target | Actual |
|---|---|---|---|---|---|---|---|
| deoxynivalenol | 0.9996 | 900 | 40 | 20 | 2.1 | 70 to 110 | 45.9 |
| aflatoxin B1 | 0.9997 | 100 | 1.6 | 20 | 1.8 | 70 to 110 | 106.8 |
| ochratoxin A | 0.9995 | 50 | 1.6 | 20 | 2.8 | 70 to 110 | 94.7 |
| T-2 toxin | 0.9988 | | 1.6 | 30 | 1.5 | 70 to 110 | 109.8 |
| HT-2 toxin | 0.9995 | | 40 | 30 | 1.4 | 70 to 110 | 109.4 |
| fumonisin B1 | 0.9959 | 5000 | 320 | 20 | 7.1 | 70 to 110 | 107.3 |
| zearalenone | 0.9997 | 100 | 40 | 25 | 2.3 | 70 to 110 | 109.8 |

TABLE 20

Analyte recovery and limit of quantitation data for a range of mycotoxins from composite horse feed using the ISOLUTE Myco protocol

| Analyte | | LOQ/μg kg$^{-1}$ | | % RSD$_r$ | | Recovery % | |
|---|---|---|---|---|---|---|---|
| Horse feed | r$^2$ | Target | Actual | Target | Actual | Target | Actual |
| deoxynivalenol | 0.9996 | 900 | 40 | 20 | 2.2 | 70 to 110 | 84.8 |
| aflatoxin B1 | 0.9990 | 100 | 1.6 | 20 | 8.1 | 70 to 110 | 100.9 |
| ochratoxin A | 0.9989 | 50 | 1.6 | 20 | 5.2 | 70 to 110 | 85.9 |
| T-2 toxin | 0.9991 | | 1.6 | 30 | 1.7 | 70 to 110 | 109.4 |
| HT-2 toxin | 0.9998 | | 40 | 30 | 5.0 | 70 to 110 | 105.0 |
| fumonisin B1 | 0.9925 | 5000 | 400 | 20 | 6.5 | 70 to 110 | 89.2 |
| zearalenone | 0.9992 | 100 | 40 | 25 | 4.9 | 70 to 110 | 108.8 |

Example 12—Extraction of Multiple Mycotoxins from Chili Using ISOLUTE® Myco Prior to LC-MS/MS Analysis This application note describes a solid phase extraction (SPE) protocol for the extraction of a range of mycotoxins from chili (pimiento) using ISOLUTE Myco with LC-MS/MS analysis.

Analytes

Aflatoxin B1, aflatoxin B2, aflatoxin G1, aflatoxin G2, ochratoxin A

Sample Preparation Procedure

Column configuration: ISOLUTE® Myco 60 mg/3 mL (Tabless), part number 150-0006-BG Sample Pre-Treatment:
1. Sample processing: Grind the sample (chili, 50 g). Store ground sample in a sealed container at 2 to 8° C. until required.
2. Extraction: Mix the ground sample (5 g) with acetonitrile:water (80:20, v/v, 20 mL) and place on a shaking table for 30 minutes. Transfer the extract to a 50 mL centrifuge tube and centrifuge at 3000 g for 10 minutes.
3. Dilution: Take the supernatant (4 mL), transfer to a new 50 mL centrifuge tube and dilute with water (28 mL) to a total volume of 32 mL. Centrifuge diluted extract at 3000 g for a further 10 minutes.

Solid Phase Extraction

As in Example 10 but the drying step was done for 30 seconds at maximum vacuum, −0.5 bar/7 psi and a second elution step used 1.0% ammonia (conc.) in methanol (2 mL).

HPLC Conditions

As in Example 10.

TABLE 21

Typical retention times for a range of mycotoxins using the LC-MS/MS method described.

| Compound | Retention time (min) |
|---|---|
| deoxynivalenol | 0.7 |
| aflatoxin B1 | 4.1 |
| HT-2 | 5.0 |
| T-2 | 5.6 |
| fumonisin B1 | 5.4 |
| zearalenone | 5.9 |
| ochratoxin A | 6.1 |

MS Conditions

Ions were selected in order to achieve maximum sensitivity, and the MS was operated in positive ion polarity mode, using multiple reaction monitoring.

TABLE 22

Positive Ion Mode - MRM Parameters

| MRM transition | RT | Compound ID | DP, V | EP, V | CE, V | CXP, V |
|---|---|---|---|---|---|---|
| 331.1 > 313.1 | 3.3 | aflatoxin G2 1 | 100 | 10 | 33 | 12 |
| 331.1 > 245.1 | 3.3 | aflatoxin G2 2 | 100 | 10 | 41 | 12 |
| 331.1 > 257.1 | 3.3 | aflatoxin G2 3 | 100 | 10 | 41 | 12 |
| 329 > 243.1 | 3.6 | aflatoxin G1 1 | 80 | 10 | 37 | 12 |
| 329 > 200 | 3.6 | aflatoxin G1 2 | 80 | 10 | 53 | 12 |
| 315.1 > 287 | 3.6 | aflatoxin B2 1 | 100 | 10 | 35 | 12 |
| 315.1 > 259.1 | 3.9 | aflatoxin B2 2 | 100 | 10 | 40 | 12 |
| 315.1 > 243.1 | 3.9 | aflatoxin B2 3 | 100 | 10 | 51 | 12 |
| 313.1 > 285 | 4.1 | aflatoxin B1 1 | 100 | 10 | 31 | 18 |
| 313.1 > 241.1 | 4.1 | aflatoxin B1 2 | 100 | 10 | 49 | 18 |
| 313.1 > 185 | 4.1 | aflatoxin B1 3 | 100 | 10 | 65 | 18 |
| 404.1 > 239 | 6.1 | ochratoxin A 1 | 165 | 10 | 32 | 12 |
| 404.1 > 221 | 6.1 | ochratoxin A 2 | 165 | 10 | 47 | 12 |
| 404.1 > 102 | 6.1 | ochratoxin A 3 | 165 | 10 | 84 | 12 |

Validation Criteria

Method linearity was determined using matrix-matched calibration standards in six replicates over six levels; the ranges are shown below.

| Analytes | Working Range, μg kg$^{-1}$ (pg μL$^{-1}$ on-column) |
|---|---|
| aflatoxin B1, aflatoxin B2, aflatoxin G1, aflatoxin G2, | 0.5 to 80 (0.046875 to 7.5) |
| ochratoxin A | 5.0 to 80 (0.46875 to 7.5) |

LOQ was determined from the lowest matrix-matched standard meeting EU repeatability and recovery criteria; or estimated from the S/N ratio of the blank where incurred levels of mycotoxins were present in the sample (e.g AB1).

Repeatability (% RSD$_r$) was determined from single acquisitions of 4 SPE replicates of a single sample extraction. The RSDs generated gave close agreement when a single sample was extracted.

Recovery was determined as a % of ISOLUTE Myco extract spike before sample prep to spike after at the EU MRL.

Results

Figure 9:
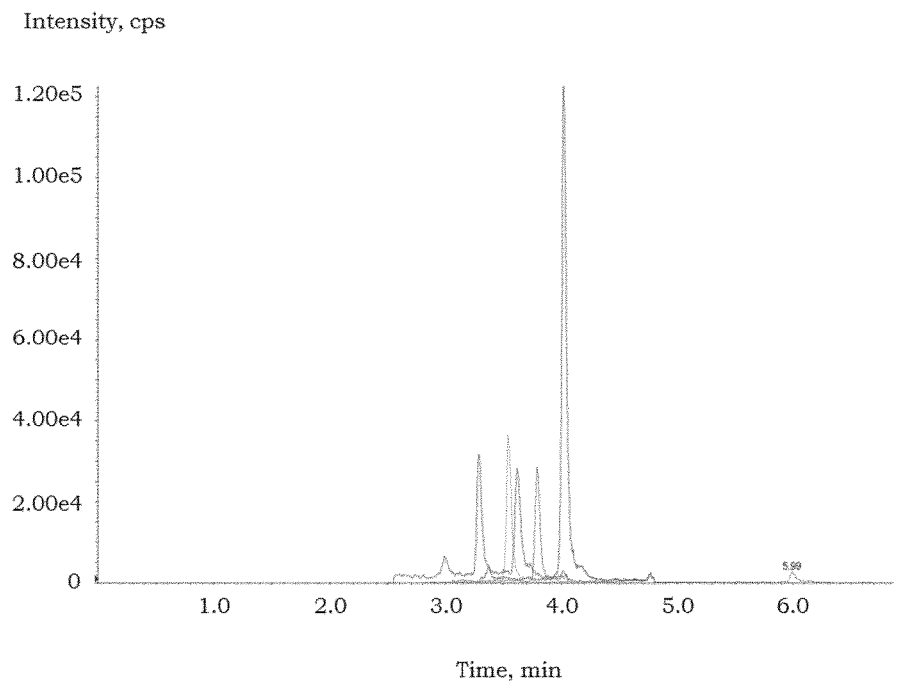
FIG. 9, shows extracted ion chromatogram (positive ion mode) using ISOLUTE Myco protocol at 5 µg $kg^{-1}$ (aflatoxins and ochratoxin A) from chili.
Figure 10:
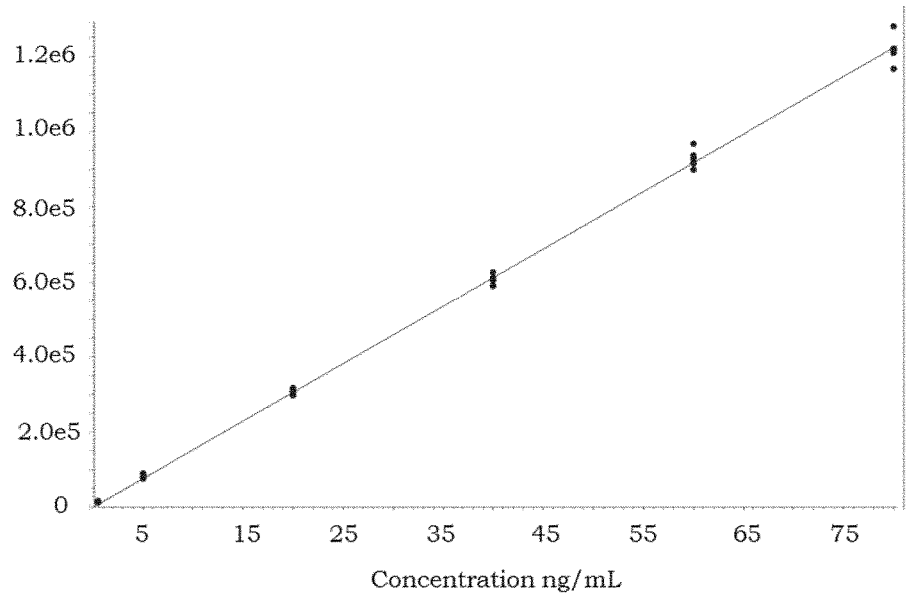
FIG. 10, Calibration curve for aflatoxin B1 from ground chili using the ISOLUTE Myco protocol from 0.5-80 µg $kg^{-1}$ FIG. 11 Calibration curve for ochratoxin A from ground chili using the ISOLUTE Myco protocol from 5-80 µg $kg^{-1}$
Figure 11:
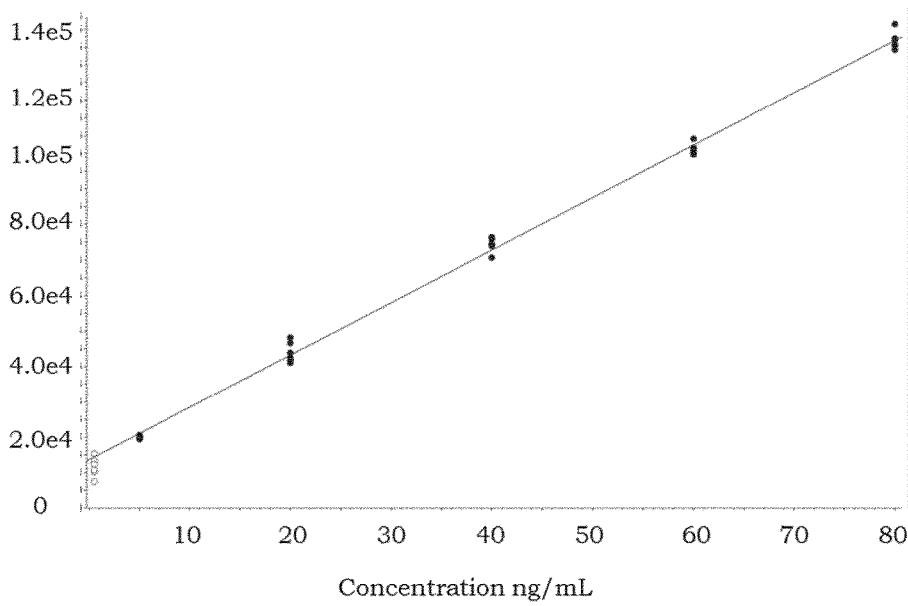

The extracted ion chromatogram in FIG. 9 demonstrates chromatography at 5 μg kg$^{-1}$ (aflatoxins and ochratoxin A) from a spiked extraction of 2 g ground chili. Good linearity was achieved for all analytes in all both matrices as demonstrated in the example charts shown in FIGS. 10 and 11.

All analytes extracted using the ISOLUTE Myco protocol achieved the limits of quantities and recovery required by the current European standards for mycotoxin analysis as shown in table 23.

TABLE 23

Analyte recovery and limit of quantitation data for a range of mycotoxins from chili using the ISOLUTE Myco protocol.

| Analyte | $r^2$ | LOQ/μg kg$^{-1}$ Target | LOQ/μg kg$^{-1}$ Actual | % RSD$_r$ Target | % RSD$_r$ Actual | Recovery % Target | Recovery % Actual |
|---|---|---|---|---|---|---|---|
| aflatoxin B1 | 0.9988 | 5 | 1.0 | 20 | 14.6 | 70 to 110 | 79 |
| aflatoxin B2 | 0.9992 | 5 | 1.0 | 20 | 8.1 | 70 to 110 | 110 |
| aflatoxin G1 | 0.9986 | 5 | 0.5 | 20 | 17.9 | 70 to 110 | 98 |
| aflatoxin G2 | 0.9980 | 5 | 0.5 | 20 | 8.6 | 70 to 110 | 104 |
| ochratoxin A | 0.9972 | 15 | 5 | 20 | 3.4 | 70 to 110 | 104 |

The invention claimed is:

1. A solid phase extraction sorbent, comprising:
a core portion, wherein the core portion includes a core bead, the core bead including styrene and divinyl benzene (DVB); and
an outermost portion,
wherein the core portion and the outermost portion of the sorbent include different compositions of one or more polymers, the composition of one or more polymers of the core portion and the composition of one or more polymers of the outermost portion each including a cross-linked polymer, the cross-linked polymer including a polymerized imidazole-based monomer,
wherein a weight ratio of the cross-linked polymer included in the outermost portion to the core bead is at least 0.05.

2. The sorbent according to claim 1, wherein the polymerized imidazole-based monomer in the cross-linked polymer has a weight that is a proportion of a weight of the cross-linked polymer, the proportion being at least 20%.

3. The sorbent of claim 2, wherein the proportion is at least 50%.

4. The sorbent of claim 3, wherein the proportion is at least 75%.

5. The sorbent according to claim 1, wherein the polymerized imidazole-based monomer includes 1-vinylimidazole.

6. The sorbent of claim 1, wherein the weight ratio is at least 0.10.

7. The sorbent of claim 6, wherein the weight ratio is at least 0.20.

8. The sorbent of claim 7, wherein the weight ratio is at least 0.33.

9. The sorbent of claim 8, wherein the weight ratio is at least 0.50.

10. A method of producing a solid phase extraction sorbent, the method comprising:
forming a mixture, the mixture including
an imidazole-based monomer,
a cross-linking agent,
a solvent, and
a polymerisation initiator;
polymerizing the mixture to form a sorbent, the polymerizing being based on combining the mixture with pre-formed beads and a stabilizer, the pre-formed beads including styrene and divinyl benzene (DVB), the sorbent including a core portion and an outermost portion, the core portion including the pre-formed beads, the core portion and the outermost portion of the sorbent including different compositions of one or more polymers, the composition of one or more polymers of the core portion and the composition of one or more polymers of the outermost portion each including a cross-linked polymer, the cross-linked polymer including a polymerized imidazole-based monomer; and
isolating the sorbent from the polymerized mixture.

11. A method of solid phase extraction (SPE) for of extracting a polar compound from a sample, the method comprising:
bringing a sorbent in contact with the sample such that the polar compound binds to the sorbent, the sample being in a liquid phase, the sorbent including a core portion and an outermost portion, the core portion being a core bead, the core bead including styrene and divinyl benzene (DVB), the core portion and the outermost portion of the sorbent including different compositions of one or more polymers, the composition of one or more polymers of the core portion and the composition of one or more polymers of the outermost portion each including a cross-linked polymer, the cross-linked polymer including a polymerized imidazole-based monomer; and eluting the polar compound from the sorbent.

12. The method according to claim 11, wherein the polar compound is a mycotoxin.

13. A solid phase extraction (SPE) cartridge, comprising:
a housing structure including openings at opposite ends; and
a sorbent within an interior of the housing structure and between the openings at the opposite ends of the housing structure, the sorbent including
a core portion, wherein the core portion includes a core bead, the core bead including styrene and divinyl benzene (DVB); and
an outermost portion,
wherein the core portion and the outermost portion include different compositions of one or more polymers, the composition of one or more polymers of the core portion and the composition of one or more polymers of the outermost portion each including a cross-linked polymer, the cross-linked polymer including a polymerized imidazole-based monomer.

* * * * *